United States Patent [19]
Epstein et al.

[11] Patent Number: 5,968,908
[45] Date of Patent: Oct. 19, 1999

[54] RESTRICTED 9-CIS RETINOIDS

[75] Inventors: Joseph William Epstein, Monroe, N.Y.; Feng Ling Qing, Shanghai, China; Gary Harold Birnberg, Monroe; Adam Matthew Gilbert, Valley Cottage, both of N.Y.

[73] Assignee: American Cyanamid Company, Madison, N.J.

[21] Appl. No.: 08/542,146

[22] Filed: Nov. 14, 1995

Related U.S. Application Data

[63] Continuation-in-part of application No. 08/359,141, Dec. 19, 1994.

[51] Int. Cl.⁶ .......................... A01N 43/04; A01N 43/40; C07D 307/87; C07D 404/00; C07D 277/04; C07C 255/00; C07C 63/00; C07C 233/00

[52] U.S. Cl. .......................... 514/42; 514/277; 514/337; 514/342; 514/364; 514/461; 514/510; 514/520; 514/535; 514/569; 514/617; 514/621; 514/650; 549/462; 549/467; 549/13; 549/356; 549/427; 549/469; 549/470; 546/284; 546/309; 548/183; 558/388; 558/410; 560/55; 560/59; 560/102; 562/405; 562/466; 562/492; 465/169; 465/180; 568/807; 568/808

[58] Field of Search ..................................... 568/807, 808; 546/462, 467, 469, 470, 13, 356, 427, 284.1, 309; 548/183; 558/388, 410; 560/55, 59, 102; 502/405, 466, 492; 564/169, 180; 514/42, 277, 337, 342, 369, 401, 510, 520, 535, 569, 617, 621, 650

[56] References Cited

FOREIGN PATENT DOCUMENTS

| 94112461 | 8/1994 | European Pat. Off. . |
| 95110460 | 7/1995 | European Pat. Off. . |
| WO 9605165 | 2/1996 | WIPO .............................. C07C 57/50 |

OTHER PUBLICATIONS

Rottman, J. N., et al., Molecular and Cellular Biology, 11, No. 7, 3814–20, 1991.

Gollnick, H., et al., Saurat (ed.) Retinoids: New Treads in Research and Therapy, Retinoid Symposium, Geneva 1984, 445–460 (Kargar, Base 1985).

Zhang, X. et al., Nature, 358, 587–591, 1992.

Jong, L. et al., J. Med. Chem., 36, 2605–2613, 1993.

*Primary Examiner*—John Kight
*Assistant Examiner*—Raymond Covington
*Attorney, Agent, or Firm*—Michael R. Nagy

[57] ABSTRACT

The invention is novel analogs of 9-cis-retinoic acid which are useful for the treatment and prevention of coronary artery disease and to protect against premature atherosclerosis by increasing HDL levels. The invention includes processes for preparing the novel 9-cis-retinoic acid analogs.

33 Claims, No Drawings

RESTRICTED 9-CIS RETINOIDS

This is a continuation-in-part of U.S. Ser. No. 08/359,141, filed Dec. 19, 1994.

BACKGROUND OF THE INVENTION

1. Field of the Invention
2. Description of the Prior Art

The family of molecules comprising both the natural and synthetic analogs of retinol (Vitamin A), are potent agents for control of both cellular differentiation and cellular proliferation (Wolbach et al, *J. Exp. Med.*, 42:753–777). High Density Lipoproteins (HDL), a heterogeneous population of spherical particles containing variable amounts of lipids and apolipoprotein, are the most abundant lipoproteins in the plasma. It has recently been observed that low plasma HDL levels are associated with an increased incidence of coronary artery disease (CAD). Numerous epidemiological studies over the last thirty years have verified this association and provided evidence for a putative protective effect of increased HDL levels against CAD (Miller, N. E., *Am Heart J*, 113:589–597 (1987). It is believed that HDL plays a fundamental role in the lipid transport system and that HDL represents a site for transport storage of potentially harmful lipids and apolipoproteins which, if they were not packaged into lipoprotein particles, might damage cell membranes because of their potential detergent properties (Eisenberg, S., *J. Lipid Res.* 25:1017–1058 (1984)).

It is known that high-density lipoproteins are involved in a large number of diverse intravascular metabolic processes including the process of reverse cholesterol transport, in which cholesterol from extrahepatic tissue is transported to the liver for conversion to bile acids and eventual excretion. As a result of the observations, research efforts have focused on methods of affecting plasma HDL levels in order to provide protection against CAD.

As stated above, spherical particles of HDL contain variable amounts of lipoproteins and apolipoproteins. Apolipoprotein A-I (Apo A-I) is a major protein constituent of plasma HDL and intestinally derived lipoproteins known as chylomicrons. Although recent studies suggest that dietary, hormonal and other environmental factors regulate Apo A-I gene expression, the molecular basis for the mechanisms involved remains poorly understood. It is known that the gene coding for apolipoprotein A-I is expressed predominantly in the liver and intestine. Previous work has shown that hepatocyte-specific expression is determined by synergistic interactions between transcription factors bound to three separate sites with a powerful liver-specific enhancer located on the −222 to −110 nucleotides upstream of the apolipoprotein A-I start site (Widom et al, *Mol. Cell Biol.*, 11:677–678 (1991)). In a recent study, it was found that one of the sites in this enhancer is a highly specific retinoic acid-responsive element, RARE, that responds to recently identified retinoic acid receptors, RXRα, (Rottman et al, *Mol. Cell Biol.*, 11:3814–3820 (July 1991). These results suggest that retinoic aid response pathways mediated by RXRα play a role in apolipotrotein A-I expression and ultimately cholesterol and retinoid transport and metabolism.

Ringer el al, *Am. J. Chem. Nutr.*, 53:688–694 (1991) observed an increase in HDL concentrations in patients given β-carotene, but did not find any changes in apolipoprotein A or B levels. Gollinich et al, Saurat (ed.), *Retinoids: New Finds in Research and Therapy*, Retinoid Symp., Geneva 1984, pp 445–460 (Karger, Basel 1985) reported no significant alteration in the HDL and LDL fractions of cholesterol in patients given etretinoate, and a decrease in HDL-chlolesterol under isotretinoin. Lyons et al, *Br. J. Dermotology*, 107:591–595 (1982) observed a decrease in HDL-cholesterol levels in patients given 13-cis-retinoic acid.

SUMMARY OF THE INVENTION

The invention is novel analogs of 9-cis-retinoic acid which are useful for the treatment and prevention of coronary artery disease and to protect against premature atherosclerosis by increasing HDL levels. Additionally, compounds of this invention are useful in the treatment of cancers by the induction of tumor cell differentiation. The invention includes processes for preparing the novel 9-cis-retinoic acid analogs.

Compounds of the invention are represented by Formula I:

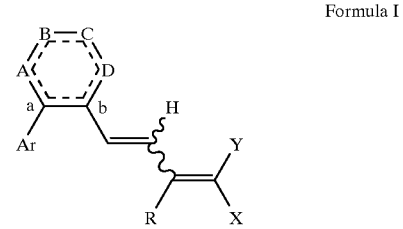

Formula I wherein:

A, B and C are CH, $CH_2$, O, or S wherein no more than one heteroatom is present;

D is $(CH)_m$, and m is an integer 0 to 1; or D is $(CH_2)_n$, and n is an integer 0 to 2;

the dotted line ,----, represents the presence or absence of a double bond whereby if only one double bond is present, it is disposed to the a-b position; or if multiple double bonds are present they are in a conjugated position to produce an aromatic ring;

R is hydrogen, methyl, ethyl, t-butyl, or trifluoromethyl;

Ar is:
a moiety of the formula:

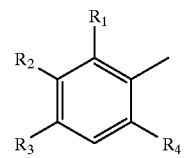

wherein $R_1$, $R_2$, $R_3$, and $R_4$ are hydrogen, $(C_1-C_3)$ alkyl, $(C_1-C_3)$alkoxy or trifluoromethyl;

a moiety of the formula:

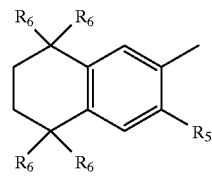

wherein $R_5$ is hydrogen, $(C_1-C_3)$alkyl, methoxy or trifluoromethyl; and $R_6$ is hydrogen, methyl or ethyl;

3 or a moiety of the formula:

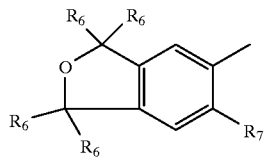

wherein $R_6$ is hydrogen, methyl or ethyl; and $R_7$ is hydrogen, methyl or ethyl; Y is hydrogen, and X is $CH_2OH$; CHO; $CO_2H$; CN; $CH_2CONH_2$ or a moiety of the formula:

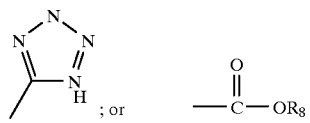

wherein $R_8$ is straight or branched $(C_1-C_8)$alkyl, or

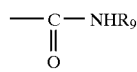

wherein $R_9$ is hydrogen, straight or branched $(C_1-C_{10})$ alkyl, glycosyl, 2-methoxyethyl, 2-dimethylaminoethyl, (1,2 or 3)-pyridyl, or (1,2 or 3)-pyridylmethyl; or X and Y taken together form the thiazolidinedione ring of the formula:

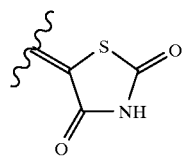

and the pharmaceutically acceptable salts and esters.

A preferred embodiment of compounds of Formula I is:

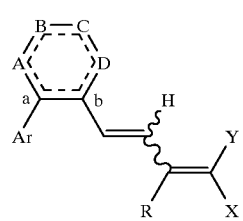

Formula I wherein:
A, B and C are CH, $CH_2$, O, or S wherein no more than one heteroatom is present;
D is $(CH)_m$, and m is an integer 0 to 1; or D is $(CH_2)_n$, and n is an integer 0 to 2;
the dotted line, -----, represents the presence or absence of a double bond whereby if only one double bond is present, it is disposed to the a-b position; or if multiple double bonds are present they are in a conjugated position to produce an aromatic ring;
R is hydrogen, methyl, ethyl, t-butyl, or trifluoromethyl;
Ar is:

4 a moiety of the formula:

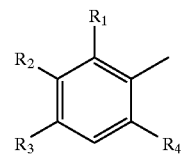

wherein $R_1$, $R_2$, $R_3$, and $R_4$ are hydrogen, $(C_1-C_3)$ alkyl, $(C_1-C_3)$alkoxy or trifluoromethyl; Y is hydrogen, and X is $CH_2OH$, CHO, $CO_2H$, CN, $CH_2CONH_2$, or a moiety of the formula:

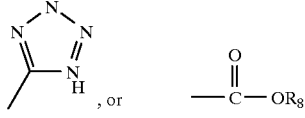

and $R_8$ is straight or branched $(C_1-C_8)$alkyl, or

wherein $R_9$ is hydrogen, straight or branched $(C_1-C_{10})$ alkyl, glycosyl, 2-methoxyethyl, 2-dimethylaminoethyl, (1,2 or 3)-pyridyl, or (1,2 or 3)-pyridylmethyl; or X and Y taken together form the thiazolidinedione ring of the formula:

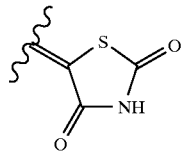

and the pharmaceutically acceptable salts and esters.
Additional preferred embodiments of Formula I are:

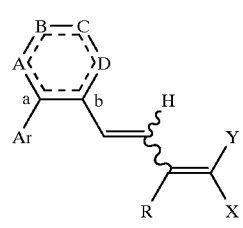

Formula I wherein:
A, B and C are CH, $CH_2$, O, or S wherein no more than one heteroatom is present;
Y is hydrogen;
D is $(CH)_m$, and m is an integer 0 to 1; or D is $(CH_2)_n$, and n is an integer 0 to 2;
the dotted line, -----, represents the presence or absence of a double bond whereby if only one double bond is present, it is disposed to the a-b position; or if multiple double bonds are present they are in a conjugated position to produce an aromatic ring;
R is hydrogen, methyl, ethyl, t-butyl, or trifluoromethyl;
Ar is:

a moiety of the formula:

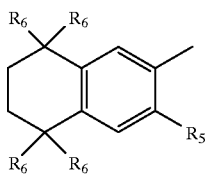

wherein $R_5$ is hydrogen, $(C_1-C_3)$alkyl, methoxy, or trifluoromethyl;
$R_6$ is hydrogen, methyl or ethyl; Y is hydrogen, and X is $CH_2OH$, CHO, $CO_2H$, CN, $CH_2CONH_2$, or a moiety of the formula:

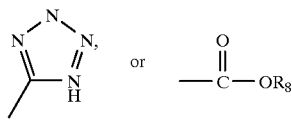

and $R_8$ is straight or branched $(C_1-C_8)$alkyl, or

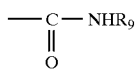

wherein $R_9$ is hydrogen, straight or branched $(C_1-C_{10})$alkyl, glycosyl, 2-methoxyethyl, 2-dimethylaminoethyl, (1,2 or 3)-pyridyl, or (1,2 or 3)-pyridylmethyl; or X and Y taken together form the thiazolidinedione ring of the formula:

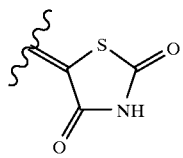

and the pharmaceutically acceptable salts and esters.
Further preferred embodiments of Formula I are:

Formula I

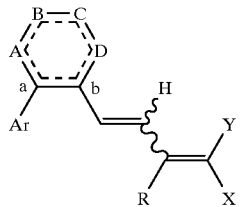

wherein:
A, B and C are CH, $CH_2$, O, or S wherein no more than one heteroatom is present;

Y is hydrogen;

D is $(CH)_m$, and m is an integer 0 to 1; or D is $(CH_2)_n$, and n is an integer 0 to 2;

the dotted line, -----, represents the presence or absence of a double bond whereby if only one double bond is present, it is disposed to the a-b position; or if multiple double bonds are present they are in a conjugated position to produce an aromatic ring;

R is hydrogen, methyl, ethyl, t-butyl, or trifluoromethyl;

Ar is:
a moiety of the formula:

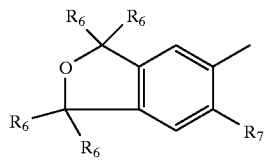

wherein $R_6$ is hydrogen, methyl or ethyl; and
$R_7$ is hydrogen, methyl or ethyl; Y is hydrogen, and X is $CH_2OH$, CHO, $CO_2H$, CN, $CH_2CONH_2$, or a moiety of the formula:

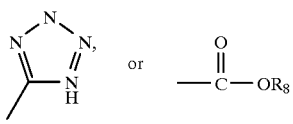

and $R_8$ is $(C_1-C_8)$alkyl, or

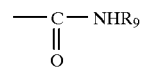

wherein $R_9$ is hydrogen, straight or branched $(C_1-C_{10})$ alkyl, glycosyl, 2-methoxyethyl, 2-dimethylaminoethyl, (1,2 or 3)-pyridyl, or (1,2 or 3)-pyridylmethyl; or X and Y taken together form the thiazolidinedione ring of the formula:

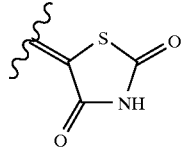

and the pharmaceutically acceptable salts and esters.

DESCRIPTION OF THE PREFERRED EMBODIMENT

According to Scheme 1,

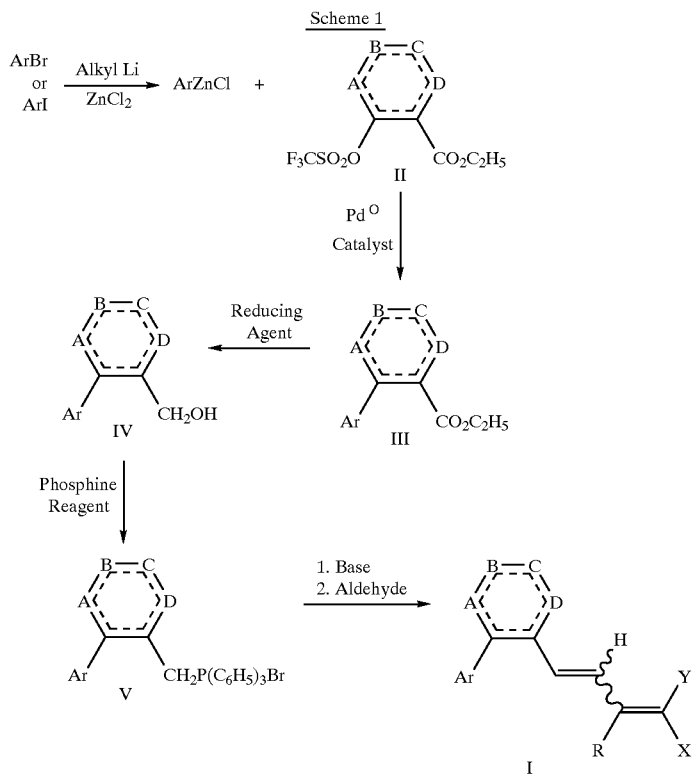

a compound of formula ArBr or ArI, wherein Ar is as defined hereinabove; is reacted with an alkyllithium such as tert-butyllithium, in an inert solvent such as tetrahydrofuran, at a temperature of −78° C. to 30° C., for 1 to 5 hours, followed by $ZnCl_2$; to give a compound of the formula:

ArZnCl which is in turn reacted with a compound of the formula II:

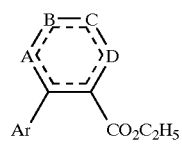

Formula II wherein A, B, C, D and the dotted line (---) are as defined hereinabove; in the presence of a palladium⁰ catalyst such as $Pd[P(C_6H_5)_3]_4$; in an inert solvent such as tetrahydrofuran; at 10 to 60° C. for 1 to 5 hours; to give a compound of Formula III:

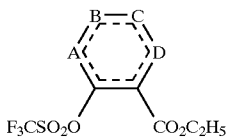

Formula III

A compound of Formula III, wherein Ar, A, B, C, D and the dotted line (---) are as defined hereinabove; is reduced with a hydride reducing agent such as lithium aluminum hydride; in an inert solvent such as diethyl ether or tetrahydrofuran; at 0 to 60° C. for 0.5 to 6.0 hours; to give a compound of Formula IV:

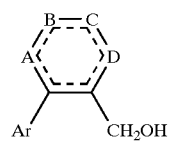

Formula IV

A compound of Formula IV, wherein Ar, A, B, C, D and the dotted line (---) are as defined hereinabove; is reacted with a phosphine such as triphenylphosphine hydrobromide; to give a compound of Formula V:

Formula V

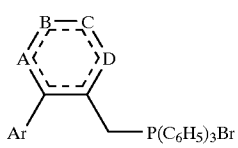

A compound of formula V is reacted with a base such as potassium hydroxide, sodium methoxide or sodium ethoxide; in a solvent such as methyl alcohol, ethyl alcohol or tetrahydrofuran; at 0° C. for 0.5 to 3.0 hours followed by the addition of an aldehyde such as

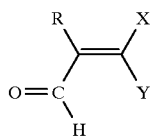

wherein R is as defined hereinabove; X is $CO_2R_8$ and $R_8$ is as defined hereinabove, y is hydrogen; to give a compound of Formula I.

According to Scheme 2, a compound of Formula I

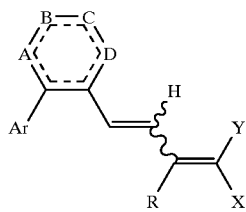

wherein Ar, A, B, C, D, R, Y, and the dotted line (---) are as defined hereinabove; X is —$CO_2H$ or —$CO_2R_8$ and $R_8$ is as defined hereinabove; is reacted with a hydride reducing agent such as lithium aluminum hydride; in an inert solvent such as tetrahydrofuran; at 0 to 60° C. for 0.5 to 3.0 hours; to give a compound of Formula I wherein X is —$CH_2OH$. The resulting compound is then reacted with an oxidizing agent such as manganese dioxide to give a compound of Formula I wherein X is —CHO, and Y is hydrogen.

Scheme 2

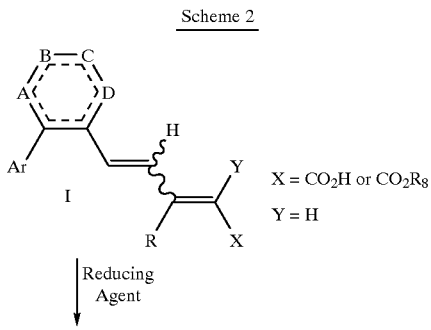

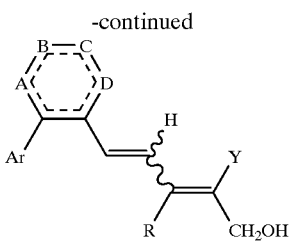

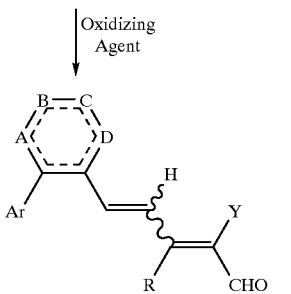

Alternatively, as shown in Scheme 3, a compound of Formula I, wherein Y is hydrogen; X is —$CO_2R_8$ and $R_8$ is as defined hereinabove, is reacted under hydrolysis conditions with a base such as sodium hydroxide or potassium hydroxide in water; at 30 to 100° C. for 0.5 to 8 hours; followed by acidification with a mineral acid such as hydrochloric acid; to give a compound of Formula I wherein X is —$CO_2H$.

Scheme 3

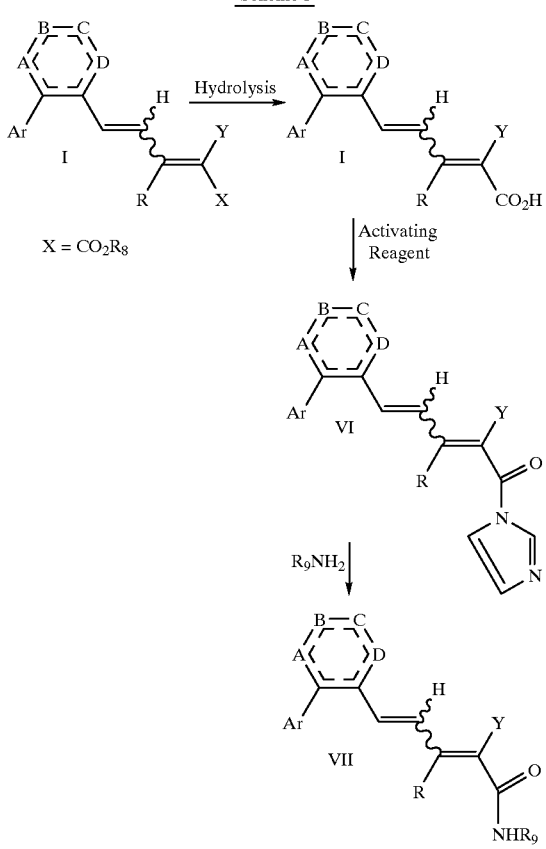

A compound of Formula I wherein Ar, A, B. C, D, the dotted line (---) and R and Y are as defined hereinabove and X is —CO$_2$H, is reacted with an activating reagent selected from carbonyldiimidazole, thionyl chloride, t-butylchloroformate, PCl$_3$, POCl$_3$, and PCl$_5$; in a solvent such as tetrahydrofuran; at 0 to 25° C. for 0.5 to 1 hour; to give an intermediate of the Formula VI when the activating reagent is carbonyldiimidazole:

Formula VI

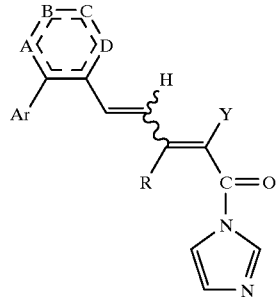

to which is added an amine of the formula R$_9$NH$_2$, wherein R$_9$ is as defined hereinabove, to give an amide of Formula VII:

Formula VII

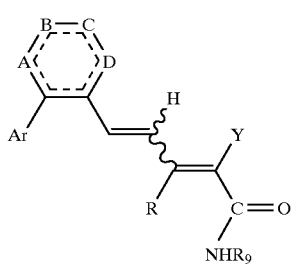

wherein Ar, A, B, C, D, Y, the dotted line (---) and R9 are as defined hereinabove.

According to Scheme 4, a compound of Formula IV:

Formula IV

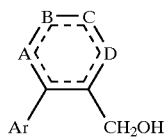

wherein Ar, A, B, C, D and the dotted line (---) are as defined hereinabove; is oxidized with a reagent such as activated MnO$_2$; in a solvent such as methylene chloride; at 0° C. to 40° C. for 0.5 to 6.0 hours; to give a compound of Formula VIII:

Formula VIII

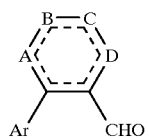

which is reacted with an ylide such as

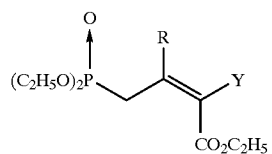

wherein R is hydrogen, methyl, t-butyl or trifluoromethyl; in the presence of a base such as sodium hydride; in an inert solvent such as tetrahydrofuran; to give a compound of Formula I wherein A, B, C, D, Ar, the dotted line (---) and R are as defined hereinabove and X is CO$_2$C$_2$H$_5$.

Scheme 4

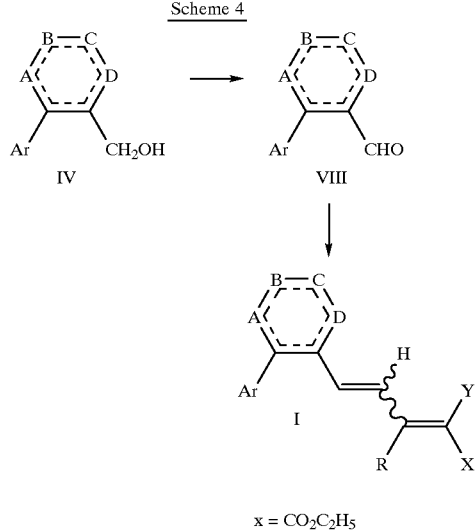

x = CO$_2$C$_2$H$_5$

Scheme 5

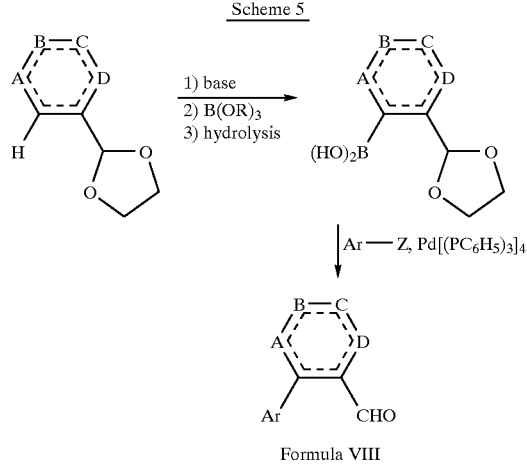

Formula VIII

According to Scheme 5, a ketal of the above formula wherein A, B, C, and D are as defined above is reacted with a base such as n-butyllithium in a solvent such as tetrahydrofuran at −78° C. to 0° C., followed by the addition of a borate ester such as triisopropylborate and then hydrolysis to a boronic acid. The boronic acid is reacted with an aryl halide of formula ArZ, wherein Z is bromine or iodine in the presence of a palladium(O) catalyst such as tetrakistriph enylphosphine palladium(O) at room temperature, followed by acid hydrolysis to give an aldehyde of formula VIII.

Scheme 6

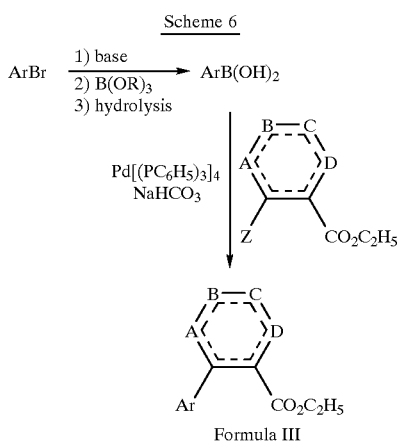

Formula III

According to Scheme 6, an aryl bromide of formula ArBr, wherein Ar is as defined above is reacted with a base such as n-butyllithium in a solvent such as tetrahydrofuran at −78° C. to 0° C., followed by the addition of a borate ester such as triisopropylborate, then hydrolysis to a boronic acid of the formula:

and this is reacted with a compound of formula:

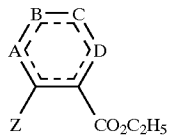

wherein A, B, C, and D are as defined above, and Z is bromine or iodine in a solvent such as dimethoxyethane in the presence of a palladium(O) catalyst, such as tetrakistriphenylphosphine palladium(O) and sodium carbonate to give a compound of Formula III as defined above.

BIOLOGY

Apolipoprotein (Apo A-I) is the major protein constituent of plasma HDL. Numerous epidemiologic, genetic and biochemical studies have provided strong support for the concept that high plasma HDL concentrations protect against premature atherosclerosis.

The physiological hormones for retinoic acid receptor (RAR) and for retinoic X receptor (RXR) are proposed to be all-trans-retinoic acid (RA) and 9-cis-retinoic acid (9-cis RA), respectively. However, 9-cis RA can bind to, and transcriptionally activate the RAR as well. In order for RARs to bind retinoic acid response elements (RAREs) and induce gene transcription effectively, they must form heterodimers with RXRs. However, in the presence of 9-cis RA, RXRs can form homodimers that bind and activate specific genes.

The novel compounds of this invention which have the ability to elevate serum levels of apolipoprotein A-I and also HDL in rats, are indicative of therapeutic agents for the treatment of conditions resulting from low HDL, such as atherosclerosis in humans.

Members of the nuclear receptor superfamily, including RXRα, activate transcription by binding to their cognate sites on the DNA located within the vicinity of the start site of the target gene (Evans, R., Science 240, 889 (1988)).

Biological Results

Electrophoretic Mobility Shift Assay

The synthetic retinoids are tested in an electrophoretic mobility shift assay (EMSA) in which the ligand dependent binding of RXRα to site A of the Apo A-I gene promoter is monitored (Rottman, J. N., MCB 11, 3814 (1991)). RXRα obtained from E. coli harboring an RXRα-expression plasmid is purified to homogeneity by affinity chromatography. For the EMSA, the purified protein is incubated with a radiolabelled oligonucleotide probe containing site A sequences in the absence or presence of the retinoid. RXRα-DNA complexes are resolved from unbound probe by electrophoresis on nondenaturing polyacrylamide gels (Fried, M. and Crothers, D. M., Nucleic Acid Research 9, 6505 (1981)).

9-cis-RA, the natural ligand for RXRα, presumably promotes binding of RXRα to the probe, by facilitating homodimer formation (Zhang, X. K., et al, Nature 358, 587 (1992)). The 9-cis-RA induced complex is specific as assessed by oligonucleotide competition and antibody supershift (Rottman, J. N., MCB 11, 3814 (1991)). Comparative potencies for test compounds is determined by visual inspection of the intensity of the autoradiograph and are shown in Table 1.

TABLE 1

| Compound Name | Potency Relative to 9-cis-RA |
|---|---|
| E,E-3-Methyl-5-[2-(5,6,7,8-tetrahydro-5,5,8,8-tetramethyl-2-naphthalenyl)-1-cyclohexen-1-yl]-2,4-pentadienoic Acid | 5+ |
| E,E-3-Methyl-5-[2-(5,6,7,8-tetrahydro-5,5,8,8-tetramethyl-2-naphthalenyl)-1-cyclopenten-1-yl]-2,4-pentadienoic Acid | 5+ |
| E,E-3-Methyl-5-[2-(5,6,7,8-tetrahydro-3,5,5,8,8-pentamethyl-2-naphthalenyl)-1-cyclopenten-1-yl]-2,4-pentadienoic Acid | 4+ |
| 3-Methyl-5-[2-(5,6,7,8-tetrahydro-3,5,5,8,8-pentamethyl-2-naphthalenyl)-phenyl]-2,4-pentadienoid Acid | 4+ |
| E,E-3-Methyl-5-[2-(3,5,5,8,8-pentamethyl-5,6,7,8-tetrahydro-2-naphthalenyl)-1-cyclohexen-1-yl]-2,4-pentadienoic Acid | 3+ |
| E,E-3-Methyl-5-[2-(1,1,3,3-tetramethyl-1,3-dihydro-5-isobenzofuranyl)-1-cyclopent-1-yl]-2,4-pentadienoic Acid | 2+ |
| 3-Methyl-5-[2-(5,6,7,8-tetrahydro-5,5,8,8-tetramethyl-2-naphthalenyl)phenyl]-2,4-pentadienoic Acid | 1+ |
| 3-Methyl-TTNEB* (Prior Art Compound) | 1+ |

*3-methyl-TTNEB (Boehm, M., et el, International Publication Number: WO 93/21146, WIPO, October 28, 1993, structure follows)

in Vivo Serum HDL and Apo A-I Assay

Male Wistar rats (190–210 g) are used in the study to measure serum levels of HDL. Compounds are suspended in sterile olive oil at a concentration of 20 mg/ml. Rats are bled by retroorbital puncture before starting the study and then given retinoids at a dose of 100 mg/kg/day by intraperitoneal injection. Total volume injected is 1 ml with 1 ml olive oil injected into vehicle animals. Rats are injected for 4 days and bled 24 hours after the last injection by heart puncture. Blood is collected in EDTA and the plasma is analyzed for HDL cholesterol, total cholesterol, and Apo A-I.

The results for E,E-3-methyl-5-[2-(5,6,7,8-tetrahydro-3,5,5,8,8-pentamethyl-2-napthalenyl)-1-cyclopenten-1-yl]-2,4-pentadienoic acid, 3-methyl-TTNEB (Boehm, M., et el, International Publication Number: WO 93/21146, WIPO, Oct. 28, 1993, structure follows), and all trans-retinoic acid are shown in Table 2 and FIGS. 1 and 2.

TABLE 2

| | Per Cent Change from Control | |
|---|---|---|
| Compound Name | HDL Cholesterol | Apo A-1 |
| E,E-3-Methyl-5-[2-(5,6,7,8-tetrahydro-3,5,5,8,8-pentamethyl-2-naphthalenyl)-1-cyclopenten-1-yl]-2,4-pentadienoic Acid | +32% | +70% |
| 3-Methyl-TTNEB (Prior Art Compound) | +41% | +4% |
| All trans-retinoic Acid (Prior Art Compound) | −9% | −71% |

Agents that induce differentiation have been proposed as alternatives to cytotoscic treatment in cancer therapy. Trans-retinoic acid has been successful in inducing remission in patients with promyelocytic leukemia [R. P. Warrell, et al., New England Journal of Medicine, Vol. 324, 1385–1393, 1991]. Compounds of this invention are tested for their ability to induce differentiation in HL-60 promyelocytic leukemia cells. CD11b expression: $2.5 \times 10^5$ HL60 cells are incubated with serial dilutions of drugs for 3 days. Cells are washed with PBA (Dulbecco's PBS (w/out $Ca^{++}$ and $Mg^{++}$), 0.1% bovine serum albumin and 0.1% sodium azide) and incubated with 1.6 μg/ml of mouse anti-human CD11b monoclonal antibody (Pharmigen, Cat#30451A) in PBA for 1 hour at 4° C. Cells are washed with PBA and incubated with a 1:50 dilution of goat anti-mouse IgG-FITC (Becton Dickinson, Cat#349031) in PBA for 1 hour at 4° C. Cells are washed twice with PBA, resuspended in PBS and analyzed in the FACSort from Becton Dickinson. The results of Table 3 show that the compounds of Example 2 and Example 4 can induce differentiation in HL-60 cells to the same degree as 9-cis-retinoic acid.

TABLE 3

| Example | Compound Name | % CD11b Positive Cells 10 μg/ml Compound |
|---|---|---|
| 2 | E,E-3-methyl-5-[2-(5,6,7,8-tetrahydro-5,5,8,8-tetramethyl-2-napthalenyl)-1-cyclohexen-1-yl]-2,4-pentadienoic acid | 50 |
| 4 | E,E-3-methyl-5-[2-(5,6,7,8-tetrahydro-5,5,8,8-tetramethyl-2-napthalenyl)-1-cyclopenten-1-yl]-2,4-pentadienoic acid | 50 |
| 6 | E,E-3-methyl-5-(2-(5,6,7,8-tetrahydro-3,5,5,8,8-pentamethyl-2-napthalenyl)-1-cyclohexen-1-yl]-2,4-pentadienoic acid | 3 |
| 8 | E,E-3-methyl-5-[2-(5,6,7,8-tetrahydro- | 5 |

TABLE 3-continued

| Example | Compound Name | % CD11b Positive Cells 10 μg/ml Compound |
|---|---|---|
| | 3,5,5,8,8-pentamethyl-2-napthalenyl)-1-cyclopenten-1-yl]-2,4-pentadienoic acid | |
| | 9-cis retinoic acid | 58 |

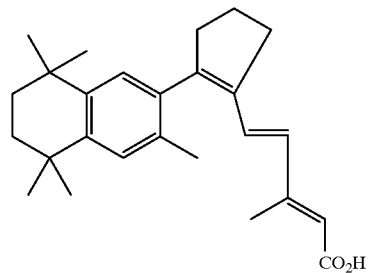

E,E-3-Methyl-5-[2-(5,6,7,8-tetrahydro-3,5,5,8,8-pentamethyl-2-naphthalenyl)-1-cyclopenten-1-yl]-2,4-pentadienoic Acid

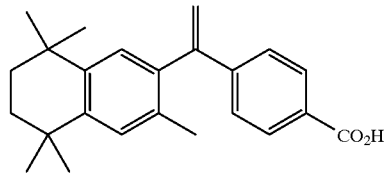

3-Methyl-TTNEB (Prior Art Compound)

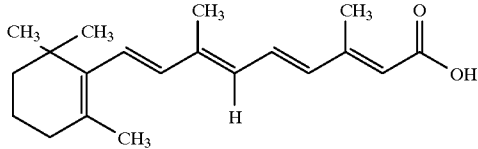

All trans-retinoic Acid (Prior Art Compound)

The compounds of Formula I may be obtained as pharmaceutically acceptable salts and esters. The salts are alkali metal salts such as sodium, potassium and lithium; alkaline earth salts such as calcium; ammonium salts; organic salts such as triethyl ammonium, morpholinium, N-methyl-morpholinium and the like. They are made using methods known to those skilled in the art (Richard C. Larock, Comprehensive Organic Transformations, VCH Publishers, 411–415, 1989). It is known to one skilled in the art that an appropriate salt form is chosen based on physical and chemical stability, flowability, hygroscopicity and solubility.

The invention compounds of Formula I may be administered orally to humans in association with a pharmaceutically acceptable carrier, for the treatment and prevention of coronary artery disease, and to protect aginst premature atherosclerosis.

When the compounds of the invention are employed for the above utility, they can be combined with one or more pharmaceutically acceptable carriers, for example, solvents, diluents and the like; and may be administered orally in such forms as tablets, capsules, dispersible powders, granules, or suspensions containing, for example, from about 0.05 to 5% of suspending agent; syrups containing, for example: from about 10 to 50% of sugar; and elixirs containing for example, from about 20 to 50% ethanol and the like, or they may be administered parenterally in the form of sterile injectable solutions or suspensions containing from about 0.05 to 5% suspending agent in an isotonic medium. Such pharmaceutical preparations may contain, for example, from about 25 to 90% of the active ingredient in combination with the carrier, and more usually, between about 5 and 60% by weight.

An effective amount of compound from 2.0 mg/kg of body weight to 100.0 mg/kg of body weight should be administered one to five times per day via any typical route of administration including, but not limited to: oral, parenteral (including subcutaneous, intravenous, intramuscular, intrasternal injection or infusion techniques), topical or rectal, in dosage unit formulations containing conventional non-toxic, pharmaceutically acceptable carriers, adjuvants and vehicles. It will be understood, however, that the specific dose level and frequency of dosage for any particular patient may be varied and will depend upon a variety of factors including: the activity of the specific compound employed, the metabolic stability and length of action of that compound, the age, body weight, general health, sex, diet, mode and time of administration, rate of excretion, drug combination, the severity of the particular condition, and the host undergoing therapy.

These active compounds may be administered orally as well as by intravenous, intramuscular, or subcutaneous routes. Solid carriers include starch, lactose, dicalcium phosphate, microcrystalline cellulose, sucrose and kaolin, which liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example: vitamin E, ascorbic acid, BHT, and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions, and sterile powders for the extemporaneous preparation of sterile injectible solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example: water, ethanol, polyol (e.g., glycerol, propylene glycol and liquid polyethylene glycol), suitable mixtures thereof, and vegetable oil.

The compounds may also be encapsulated in liposomes to allow an intravenous administration of the drug. The liposomes suitable for used in this invention are lipid vesicles and may include plurilamellar lipid vesicles, small sonicated multilamellar vesicles, reverse phase evaporation vesicles, large multilamellar vesicles and the like wherein the lipid vesicles are formed of one or more phospholipids such as phosphatidylcholine, phosphatidylglycerol, sphingomyelin, phospholactic acid and the like.

The following examples describe in detail the chemical synthesis of representative compounds of the present invention. The procedures are illustrations, and the invention should not be construed as being limited by chemical reactions and conditions that they express. No attempt has been made to optimize the yields obtained in these reactions, and it would be obvious to one skilled in the art that variations in reaction times, temperatures, solvents, and/or reagents could increase the yields.

EXAMPLE 1

Z,E and E,E-3-Methyl-5-[2-(5,6,7,8-tetrahydro-5,5, 8,8-tetramethyl-2-naphthalenyl)-1-cyclohexen-1-yl]- 2,4-pentadienoic Acid Ethyl Ester To a stirred solution of 2.0 g of 2-bromo-(5,6,7,8-tetrahydro-5,5,8,8-tetramethyl)naphthalene in 20 ml of anhydrous tetrahydrofuran at −78° C. is added 9 ml of 1.7M tert-butyllithium in pentane, followed by the addition of 15 ml of zinc chloride, 0.5M in tetrahydrofuran. The mixture is allowed to warm to room temperature, 0.39 g of tetrakistriphenyl phosphinepalladium(0) and 1.0 g of ethyl 2-trifluoromethanesulfonyloxycyclohexen-1-ylcarboxylate in 5 ml of tetrahydrofuran is added and the resulting solution is stirred for 2 hours at the reflux temperature of the solvent. The reaction is cooled to room temperature, 50 ml of diethyl ether is added and the layers are separated. The organic layer is washed with water, aqueous sodium bicarbonate, saturated sodium chloride, and dried over sodium sulfate. Evaporation of the solution, followed by chromatography (silica gel: hexane/diethyl ether 4:1) gives 1.5 g of 2-(5,6, 7,8-tetrahydro-5,5,8,8-tetramethyl-2-naphthalenyl)-1-cyclohexene-1-carboxylic acid, ethyl ester as a colorless solid.

A solution of 1.48 g of the above isolated solid in 15 ml of diethyl ether is added dropwise at 0° C. to 10 ml of 1.0N lithium aluminum hydride in anhydrous tetrahydrofuran, followed by stirring at room temperature for 15 minutes. Water is added dropwise to the cooled reaction mixture. The reaction is extracted with diethyl ether. The organic layers are combined, dried over sodium sulfate and evaporated to give the alcohol as an oil. The oil is dissolved in 60 ml of methyl alcohol to which is added 1.5 g of triphenylphosphine hydrobromide and the reaction mixture is stirred at room temperature for 17 hours. The solvent is removed in vacuo, and the residue is washed with diethyl ether to give the corresponding phosphonium bromide, and then this is dissolved in 25 ml of dry methylene chloride, cooled under argon to 0° C., and sodium ethoxide and 0.7 ml of ethyl 3-methyl-4-oxocrotonate are added. The mixture is stirred at 0° C. for 1 hour and quenched with water. The methylene chloride extract is dried over sodium sulfate, evaporated to a red oil and the oil is purified by chromatography (silica gel: hexane/diethyl ether 9:1) to give 1.1 g of a 15:2 mixture of E,E and Z,E esters.

EXAMPLE 2

E,E-3-Methyl-5-[2-(5,6,7,8-tetrahydro-5,5,8,8-tetramethyl-2-naphthalenyl)-1-cyclohexen-1-yl]-2,4-pentadienoic Acid The mixed (15:2) ester product from Example 1 is combined with 5 ml of 2N aqueous potassium hydroxide in 10 ml of methyl alcohol and stirred at reflux temperature for 3 hours. The reaction mixture is cooled to room temperature, poured into a mixture of ice and methylene chloride, and acidified to pH 3 with 3N hydrochloric acid. The organic layers are combined, dried over sodium sulfate and evaporated to give a light yellow solid. The solid is recrystallized form absolute ethyl alcohol to give 0.5 g of the desired compound as colorless crystals.

mp 198–199° C.; $^1$H NMR (CDCl$_3$): δ 1.24 (s, 6H), 1.26 (s, 6H), 1.69 (s, 4H), 1.76–1.82 (m, 4H), 2.10 (s, 3H), 2.32–2.39 (m, 2H), 2.46–2.50 (m, 2H), 5.77 (s, 1H), 6.25 (d, J=16.0 Hz, 1H), 6.86 (d, J=16.0 Hz, 1H), 6.95 (d, J=7.0 Hz, 1H), 7.06 (s, 1H), 7.28 (d, J=7.0 Hz, 1H) $^{13}$C NMR (CDCl$_3$) ppm downfield from TMS: 13.90, 22.52, 22.78, 22.91, 25.66, 31.80, 31.90, 33.05, 34.10, 34.22, 35.06, 35.14, 116.93, 125.46, 126.16, 127.56, 128.58, 129.96, 136.46, 139.26, 143.66, 144.15, 144.49, 156.33, 172.39. IR (KBr): 3054, 2959, 2928, 2861, 1593, 1679, 1595, 1491, 1457, 1363, 1349, 1262, 1188, 963, 878 cm$^{-1}$. MS (CI): m/z 379. UV (in CH$_3$OH): 317 nM.

EXAMPLE 3

Z,E and E,E-3-Methyl-5-[2-(5,6,7,8-tetrahydro-5,5,8,8,-tetramethyl-2-naphthalenyl)-1-cyclopenten-1-yl]-2,4-pentadienoic Acid Ethyl Ester Following the procedure of Example 1 using ethyl 2-trifluoromethanesulfonyloxycyclopenten-1-yl carboxylate, the title compounds are obtained as a 13:3 mixture of E,E- and Z,E- isomers which are separated and purified by chromatography to yield the individual isomers.

EXAMPLE 4

E,E-3-Methyl-5-[2-(5,6,7 8-tetrahydro-5,5,8,8-tetramethyl-2-naphthalenyl)-1-cyclopenten-1-yl]-2,4-pentadienoic Acid The title compound is prepared by the procedure of Example 2 using 1.19 g of the mixed (13:3) ester product from Example 3 to give 0.5 g of the desired product.

mp 197–198° C. $^1$H NMR (CDCl$_3$): δ 1.30 (s, 12H), 1.70 (s, 4H), 1.98–2.03 (m, 2H), 2.29 (s, 3H), 2.72 (t, J=7.0 Hz, 2H), 2.90 (t, J=7.0 Hz, 2H), 5.83 (s, 1H), 6.29 (d, J=16.0 Hz, 1H), 7.10 (d, J=7.0 Hz, 1H), 7.14 (d, J=16.0 Hz, 1H), 7.28 (s, H), 7.31 (d, J=7.0 Hz, 1H). $^{13}$C NMR (CDCl$_3$) ppm downfield from TMS: 13.90, 21.81, 22.81, 31.77, 31.86, 33.74, 34.20, 35.05, 38.70, 117.45, 125.01, 126.54, 126.88, 131.36, 132.69, 134.51, 135.23, 144.29, 144.62, 146.50, 155.83, 172.03. IR (KBr): 3447, 3314, 3052, 2958, 2926, 2865, 1679, 1592, 1457, 1436, 1414, 1386, 1363, 1281, 1256, 1186, 967, 905, 826 cm$^{-1}$. MS (CI): m/z 364 (M$^+$) UV (in CH$_3$OH): 323 nM.

EXAMPLE 5

Z,E,- and E,E-3-Methyl-5-[2-(3,5,5,8.8-pentamethyl-5,6,7,8,-tetrahydro-2-naphthalenyl)-1-cyclohexen-1-yl]-2,4-pentadienoic Acid Ethyl Ester To a stirred (−78° C.) solution of 4.2 g of 2-bromo-3,5,5,8,8-pentamethyl-5,6,7,8-tetrahydronaphthalene in 40 ml of tetrahydrofuran is added 18 ml of tert-butyllithium (1.7N in pentane). The reaction mixture is stirred at −78° C. for 1 hour, warmed to room temperature and stirred for 1 hour. Thirty ml of 0.5M zinc chloride solution in tetrahydrofuran is added and the stirring continued for 1 hour. Three grams of 2-trifluoromethanesulfonyloxycyclohexen-1-ylcarboxylate and 0.8 g of tetrakis(triphenylphosphine palladium(O) in tetrahydrofuran is added and the reaction mixture is heated at reflux temperature for 3 hours. Following the reaction work-up of Example 1, 2.75 g of 2-(3,5,5,8,8-pentamethyl-5,6,7,8,-tetrahydro-2-naphthalenyl)-1-cyclohexene-1-carboxylic acid ethyl ester is obtained. The above isolated ester is reduced to the corresponding alcohol with lithium aluminum hydride in diethyl ether, and this is then converted to the triphenylphosphonium bromide as in Example 1. Reaction of the bromide with ethyl 3-methyl-4-oxocrotonate and sodium ethoxide in methylene chloride, as in Example 1, gives the title compound as a mixture of E,E- and Z,E- esters in a 8:1 ratio. The esters are separated into the individual isomers by chromatography.

EXAMPLE 6

E,E-3-Methyl-5-[2-(3,5,5,8,8-pentamethyl-5,6,7,8-tetrahydro-2-naphthalenyl)-1-cyclohexen-1-yl]-2,4-pentadienoic Acid The title compound is prepared by the procedure of Example 2, using 1.08 g of the mixed ester (8:1) product from Example 5 to give 0.65 g of the desired product.

mp 208–209° C. $^1$H NMR (CDCl$_3$): δ 1.21 (s, 3H), 1.25 (s, 3H), 1.27 (s, 3H), 1.28 (S, 3H), 1.67 (s, 4H), 1.69–1.78 (m, 4H), 1.98 (s, 3H), 2.08 (s, 3H), 2.30–2.33 (m, 4H), 5.73 (s, 1H), 6.18 (d, J=16.0 Hz, 1H), 6.44 (d, J=16.0 Hz, 1H), 6.87 (s, 1H), 7.08 (s, 1H). $^{13}$C NMR (CDCl$_3$) ppm downfield from TMS: 13.58, 19.06, 22.64, 22.78, 24.94, 31.72, 31.77, 31.93, 32.13, 32.98, 33.91, 35.21, 116.82, 126.62, 127.70, 128.15, 130,30, 131.94, 136.00, 139.10, 141.98, 143.39, 145.03, 156.21, 171.71. IR (KBr): 3048, 3016, 2958, 2929, 2595, 1677, 1598, 1496, 1390, 1362, 1349, 1261, 1189, 963, 879 cm$^{-1}$. MS (CI): m/z 393 (M$^+$+H) UV (in CH$_3$OH): 306 nM

EXAMPLE 7

Z,E- and E,E-3-Methyl-5-[2-(2-(3,5,5,8,8-pentamethyl-5,6,7,8-tetrahydro-2-naphthalenyl)-1-cyclopenten-1-yl]-2,4-pentadienoic Acid Ethyl Ester The title compound is prepared by the procedure of Example 1 using ethyl 2-trifluoromethanesulfonyloxycyclopenten-1-yl carboxylate to give a 17:5 mixture of isomers which can be separated by chromatography into the individual isomers.

EXAMPLE 8

E,E-3-Methyl-5-[2-(3,5,5,8,8-pentamethyl-5,6,7,8-tetrahydro-2-naphthalenyl)-1-cyclopenten-1-yl-2,4-pentadienoic Acid The title compound is prepared by the procedure of Example 2 using the mixed isomer product from Example 7 to give the desired product.

mp 207–208° C. $^1$H NMR (CDCl$_3$): δ 1.25 (s, 6H), 1.29 (s, 6H), 1.67 (s, 4H), 2.02 (q, J=7.0 Hz, 2H), 2.16 (s, 3H), 2.18 (s, 3H), 2.62–2.68 (m, 2H), 2.71–2.80 (m, 2H0, 5.80 (s, 1H), 6.24 (d, J=16.0 Hz, 1H), 6.68 (d, J=16.0 Hz, 1H), 6.95 (s, 1H), 7.11 (s,1H). $^{13}$C NMR (CDCl$_3$) ppm downfield from TMS: 13.45, 19.67, 22.30, 31.55, 31.64, 32.39, 33.62, 33.70, 34.91, 38.93, 118.61, 127.38, 127.88, 129.82, 132.09, 132.37, 134.22, 136.52, 141.59, 143.55, 147.21, 152.86, 169.03. IR (KBr): 3014, 2957, 2864, 2585, 1683, 1595, 1495, 1455, 1416, 1362, 1347, 1257, 1186, 963, 909, 877 cm$^{-1}$. MS (CI): m/z 379 (M$^+$+H). UV (in CH$_3$OH): 316 nM.

EXAMPLE 9

E,E-3-Methyl-5-[2-(5,6,7,8,-tetrahydro-5,5,8,8-tetramethyl-2-naphthalenyl)-1-cyclohexen-1-yl]-2,4-pentadienoamide To one equivalent of product from Example 2 dissolved in dry tetrahydrofuran is added one equivalent of carbonyldiimidazole at 0° C. After stirring at 0° C. for 30 minutes, dry ammonia gas is bubbled into the reaction mixture and the stirring is continued for one hour at room temperature. The solvent is concentrated in vacuo and the desired product is recrystallized from ethyl alcohol.

EXAMPLE 10

N-(2-Methoxyethyl)-E,E-3-methyl-5-[2-(5,6,7,8,-tetrahydro-5,5,8,8-tetramethyl-2-naphthalenyl)-1-cyclohexen-1-yl]-2,4-pentadienoamide The title compound is prepared by the procedure of Example 9 using 2-methoxyethylamine.

Substantially following the methods described in detail hereinabove in Examples 9 and 10, the compounds listed below, Table 4, are prepared.

TABLE 4

| Example No. | Starting Acid | Reagent | Product |
|---|---|---|---|
| 11 | E,E-3-Methyl-5-[2-(5,6,7,8-tetrahydro-5,5,8,8-tetramethyl-2-napthalenyl)-1-cyclohexen-1-yl]-2,4-pentadienoic acid | 3-Aminomethyl-pyridine | N-(3-Pyridylmethyl)-E,E-3-methyl-5-[2-(5,6,7,8-tetrahydro-5,5,8,8-tetramethyl-2-napthalenyl)-1-cyclohexen-1-yl]-2,4-pentadienoamide |
| 12 | E,E-3-Methyl-5-[2-(5,6,7,8-tetrahydro-5,5,8,8-tetramethyl-2-napthalenyl)-1-cyclohexen-1-yl]-2,4-pentadienoic acid | 2-Dimethylamino-ethylamine | N-(2-Dimethylaminoethyl)-E,E-3-methyl-5-[2-(5,6,7,8-tetrahydro-5,5,8,8-tetra-methyl-2-napthalenyl)-1-cyclohexen-1-yl]-2,4-pentadienoamide |
| 13 | E,E-3-Methyl-5-[2-(5,6,7,8-tetrahydro-5,5,8,8-tetramethyl-2-napthalenyl)-1-cyclohexen-1-yl]-2,4-pentadienoic acid | 3-Aminopyridine | N-(3-Pyridyl)-E,E-3-methyl-5-[2-(5,6,7,8-tetrahydro-5,5,8,8-tetramethyl-2-napthalenyl)-1-cyclohexen-1-yl]-2,4-pentadienoamide |
| 14 | E,E-3-Methyl-5-[2-(5,6,7,8-tetrahydro-5,5,8,8-tetramethyl-2-napthalenyl)-1-cyclopenten-1-yl]-2,4-pentadienoic acid | NH$_3$ | E,E-3-Methyl-5-[2-(5,6,7,8-tetrahydro-5,5,8,8-tetramethyl-2-napthalenyl)-1-cyclopenten-1-yl]-2,4-pentadienoamide |
| 15 | E,E-3-Methyl-5-[2-(5,6,7,8-tetrahydro-5,5,8,8-tetramethyl-2-napthalenyl)-1-cyclopenten-1-yl]-2,4-pentadienoic acid | CH$_3$OCH$_2$CH$_2$NH$_2$ | N-(2-Methoxyethyl)-E,E-3-Methyl-5-[2-(5,6,7,8-tetrahydro-5,5,8,8-tetra methyl-2-napthalenyl)-1-cyclopenten-1-yl]-2,4-pentadienoamide |
| 16 | E,E-3-Methyl-5-[2-(5,6,7,8-tetrahydro-5,5,8,8-tetramethyl-2-napthalenyl)-1-cyclopenten-1-yl]-2,4-pentadienoic acid | D-glucosamine | E,E-N-(2-Deoxyglucosyl)-3-methyl-5-(2-(5,6,7,8-tetrahydro-5,5,8,8-tetramethyl-2-napthalenyl)-1-cyclopenten-1-yl]-2,4-pentadienoamide |
| 17 | E,E-3-Methyl-5-[2-(5,6,7,8-tetrahydro-5,5,8,8-tetramethyl-2-napthalenyl)-1-cyclopenten-1-yl]-2,4-pentadienoic acid | Alanine, t-butyl ester | N-[E,E-3-Methyl-5-[2-(5,6,7,8-tetrahydro-5,5,8,8-tetramethyl-2-napthalenyl)-1-cyclopenten-1-yl]-2,4-penta-dienoyl]alanine, t-butyl ester |
| 18 | E,E-3-Methyl-5-[2-(5,6,7,8-tetrahydro-5,5,8,8-tetramethyl-2-napthalenyl)-1-cyclopenten-1-yl]-2,4-pentadienoic acid | NH$_3$ | E,E-3-Methyl-5-[2-(5,6,7,8-tetrahydro-5,5,8,8-tetramethyl-2-napthalenyl)-1-cyclopenten-1-yl]-2,4-pentadienoamide |
| 19 | E,E-3-Methyl-5-[2-(3,5,5,8,8-pentamethyl-5,6,7,8-tetrahydro-2-napthalenyl)-1-cyclohexen-1-yl]-2,4-pentadienoic acid | NH$_3$ | E,E-3-Methyl-5-[2-(3,5,5,8,8-pentamethyl-5,6,7,8-tetrahydro-2-napthalenyl)-1-cyclohexen-1-yl]-2,4-pentadienoamide |
| 20 | E,E-3-Methyl-5-[2-(3,5,5,8,8-pentamethyl-5,6,7,8-tetrahydro-2-napthalenyl)-1-cyclohexen-1-yl]-2,4-pentadienoic acid | Glycine, t-butyl ester | N-[E,E-3-Methyl-5-[2-(3,5,5,8,8-pentamethyl-5,6,7,8-tetrahydro-2-napthalenyl)-1-cyclohexen-1-yl]-2,4-penta-dienoyl]glycine, t-butyl ester |
| 21 | E,E-3-Methyl-5-[2-(3,5,5,8,8-pentamethyl-5,6,7,8-tetrahydro-2-napthalenyl)-1-cyclohexen-1-yl]-2,4-pentadienoic acid | CH$_3$OCH$_2$CH$_2$NH$_2$ | N-(2-Methoxyethyl)-E,E-3-methyl-5-[2-(3,5,5,8,8-pentamethyl-5,6,7,8-tetrahydro-2-napthalenyl)-1-cyclohexen-1-yl]-2,4-pentadienoamide |
| 22 | E,E-3-Methyl-5-[2- | NH$_3$ | E,E-3-Methyl-5-[2-(3,5,5,8,8-penta- |

TABLE 4-continued

| Example No. | Starting Acid | Reagent | Product |
|---|---|---|---|
| | (3,5,5,8,8-pentamethyl-5,6,7,8-tetrahydro-2-napthalenyl)-1-cyclopenten-1-yl]-2,4-pentadienoic acid | | methyl-5,6,7,8-tetraydro-2-napthalenyl)-1-cyclopenten-1-yl]-2,4-pentadienoamide |
| 23 | E,E-3-Methyl-5-[2-(3,5,5,8,8-pentamethyl-5,6,7,8-tetrahydro-2-napthalenyl)-1-cyclopenten-1-yl]-2,4-pentadienoic acid | $CH_3OCH_2CH_2NH_2$ | N-(2-Methoxyethyl)-E,E-3-methyl-5-[2-(3,5,5,8,8-pentamethyl-5,6,7,8-tetrahydro-2-napthalenyl)-1-cyclopenten-1-yl]-2,4-pentadienoamide |
| 24 | E,E-3-Methyl-5-[2-5,6,7,8-tetrahydro-5,5,8,8-tetra-methyl--2-napthalenyl)-1-cyclohepten-1-yl]-2,4-pentadienoic acid | $CH_3OCH_2CH_2NH_2$ | N-(E,E-3-Methyl-5-[2-5,6,7,8-tetrahydro-5,5,8,8-tetramethyl-2-napthalenyl)-1-cyclohepten-1-yl]-2,4-pentadienoamide |

EXAMPLE 25

5-Bromo-1,1,3,3-tetramethyl-1,3-dihydroisobenxofuran

A solution of 5.0 g of 4-bromophthalic acid dissolved in 200 ml of absolute methyl alcohol is saturated with dry hydrogen chloride gas and allowed to stir at room temperature for 20 hours. The reaction mixture is evaporated in vacuo, kept under high vacuum overnight to give 5.13 g of dimethyl-4-bromophthalate as a pale yellow oil.

$^1$HNMR (CDCl$_3$): δ 3.90 (s, 3H); 3.92 (s, 3H); 7.62 (d, J=8.3 Hz, 1H); 7.67 (dd, J=8.3 Hz, 1.8 Hz, 1H); 7.84 (d, J=1.8 Hz, 1H)

A mixture of 27.3 g of the above product dissolved in 100 ml of tetrahydrofuran is cooled in an ice bath. To this cooled mixture is added, dropwise over 30 minutes, 200 ml of 3.0M methylmagnesium chloride in tetrahydrofuran. After the addition is completed, the reaction is heated at reflux temperature for 24 hours, quenched into 400 ml of saturated ammonium chloride, and extracted with diethyl ether. The combined organic layers are washed with saturated sodium chloride, dried over sodium sulfate, filtered and evaporated to give the crude product as an oil. The crude product is crystallized with hexane to give 9.55 g of 2,2'-(4-bromo-1,2-phenylene)bis(2-propanol).

$^1$HNMR (CDCl$_3$): δ 1.69 (s, 6H); 1.70 (s, 6H), 4.97 (brs, 2H); 7.18 (d, J=8.6 Hz, 1H); 7.28 (dd, J=8.7 Hz, 2.22 Hz, 1H); 7.44 (d, J=2. Hz, 1H).

To 26 ml of 60% sulfuric acid is added 2.92 g of the above diol product. The mixture is heated at 50° C. for 1 hour. The reaction mixture is poured into water and extracted with hexane. The combined hexane layers are washed with saturated sodium bicarbonate, saturated sodium chloride, dried over sodium sulfate, filtered through a short pad of hydrous magnesium silicate and evaporated to give 2.47 g of the desired title compound as a white solid.

$^1$HNMR (CDCl$_3$): δ 1.49 (s,6H); 1.50 (s, 6H); 6.96 (d, J=8.0 Hz, 1H) 7.22 (d, J=1.6 Hz, 1H); 7.39 (dd, 1.7 Hz, 1H).

EXAMPLE 26

E,E, and Z,E-3-Methyl-5-[2-(1,1,3,3-tetramethyl-1,3-dihydro-5-isobenzofuranyl)-1-cyclohexen-1-yl]-2,4-pentadienoic Acid, Ethyl Ester The title compound, as a mixture of E,E and Z,E isomers, is prepared by the procedure of Example 1 using the product from Example 25.

EXAMPLE 27

E,E-3-Methyl-5-[2-(1,1,3,3-tetramethyl-1,3-dihydro-5-isobenzofuranyl)-1-cyclohexen-1-yl]-2,4-pentadienoic Acid The title compound is prepared by the procedure of Example 2 using the product from Example 26.

EXAMPLE 28

Z,E and E,E-3-Methyl-5-[2-(5,6,7,8-tetrahydro-5,5,8,8-tetramethyl-2-naphthalenyl)-1-cyclohexen-1-yl]-2,4-pentadienoic Acid Methyl Ester Ethyl 2-(5,6,7,8-tetrahydro-5,5,8,8-tetramethyl-2-naphthalenyl)-1-cyclohexene-1-carboxylate described in Example 1 is stirred with excess lithium aluminum hydride in diethyl ether at reflux temperature for 3 hours. The mixture is cooled and water is added dropwise. The ether layer is dried over sodium sulfate and evaporated to give 2-(5,6,7,8-tetrahydro-5,5,8,8-tetramethyl-2-naphthalenyl)-1-cyclohexenylmethanol.

The above alcohol is stirred with excess active manganese dioxide in methylene chloride for 5 hours. The reaction mixture is filtered and evaporated to give 2-(5,6,7,8-tetrahydro-5,5,8,8-tetramethyl-2-naphthalenyl)-1-cyclohexenecarboxaldehyde.

To one equivalent of sodium hydride in tetrahydrofuran/hexamethylphosphoramide (2:1) is added one equivalent of methyl γ-dimethylphosphonomethacrylate dropwise at 0° C. and the reaction mixture is stirred at room temperature for 45 minutes. The reaction is cooled to 0° C. and one equivalent of the aldehyde described above, in dry tetrahydrofuran, is added, and the mixture is stirred at room temperature for 5 days. Water is added and the mixture is extracted with diethyl ether. The diethyl ether extract is dried over sodium sulfate, filtered and evaporated to give the title compound as a mixture of isomers.

EXAMPLE 29

3-Methyl-5-[2-(5,6,7,8-tetrahydro-3,5,5,8,8-pentamethyl-2-naphthalenyl)phenyl]-2,4-pentadienoic Acid In a manner identical to that of Example 5, 2-bromo-3,5,5,8,8-pentamethyl-5,6,7,8-tetrahydronaphthalene is reacted with ethyl 2-trifluoromethanesulfonyloxybenzoate to give ethyl 2-(3,5,5,8,8-pentamethyl-5,6,7,8,-tetrahydro-2-naphthalenylbenzoate.

To 1.0 g of the above compound in 10 ml of dry diethyl ether is added 10 ml of 1.0M lithium aluminum hydride, and after workup, as in Example 5, the alcohol is isolated. The alcohol is dissolved in methylene chloride, 6.0 g of active manganese dioxide is added and the reaction mixture is stirred at room temperature for three days. Filtration through diatomaceous earth, and evaporation gives 2-(3,5,5,8,8-pentamethyl-5,6,7,8-tetrahydronaphthalen-2-yl-benzaldehyde as a yellow oil.

To a suspension of 0.3 g of sodium hydride in 30 ml of tetrahydrofuran is added 1.42 g of methyl γ-dimethylphosphonomethacrylate at 0° C. This mixture is stirred at 20° C. for 1 hour. The above aldehyde, 1.1 g, is added and this mixture is stirred for 2 hours at room temperature. The reaction is quenched with water and the product is isolated as a mixture of E and Z isomers. Hydrolysis with potassium hydroxide, followed by acidification of the solution with dilute hydrochloric acid gives the desired product as colorless crystals.

mp=181–182° C. $^1$HNMR (CDCl$_3$): δ 1.21 (S, 3H), 1.26 (S, 3H), 1.31 (S, 3H), 1.33 (S, 3H), 1.70 (S, 4H), 2.03 (S, 3H), 2.11 (S, 3H), 5.83 (S, 1H), 6.69 (S, 1H), 6.71 (S, 1H), 7.01 (S, 1H), 7.34 (d, J=16.0 Hz, 1H), 7.38 (d, J=16.0 Hz, 1H), 7.43–7.45 (m, 1H), 7.64–7.74 (m, 1H). $^{13}$CNMR (CDCl$_3$) ppm downfield from TMS: 13.77, 19.18, 31.80, 31.99, 32.11, 33.96, 34.04, 35.34, 118.41, 125,65, 127.30, 128,17, 128.43, 130.50, 132.06, 132.84, 134.10, 134.86, 137.11, 142.11, 142.27, 144.26, 155.08, 171.96. MS (CI): m/z 389 (M$^+$+H).

EXAMPLE 30

3-Methyl-5-[2-(5,6,7,8-tetrahydro-5,5,8,8-tetramethyl-2-naphthalenyl)phenyl]-2,4-pentadienoic Acid Following the procedure of Example 29, the title compound is prepared using 2-bromo-5,5,8,8-tetramethyl-5,6,7,8-tetrahydronaphthalene.

mp=178–179° C. $^1$HNMR (CDCl$_3$): δ 1.27 (s, 6H), 1.33 (s, 6H), 1.72 (s, 4H), 2.25 (s, 3H), 5.92 (s, 1H), 6.78 (d, J=16.0 Hz, 1H), 7.14 (d, J=16.0 Hz, 1H), 7.25 (s, 1H), 7.33–7.38 (m, 1H), 7.65–7.68 (m, 1H). $^{13}$CNMR (CDCl$_3$) ppm downfield from TMS: 14.12, 17.16, 31.87, 31.93, 34.31, 35.13, 118.35, 126.29, 126.50, 126.75, 127.29; 128.44, 128.55, 130.43, 132.30, 134.38, 134.92, 137.24, 142.26, 144.05, 144.28, 155.22, 170.51.

EXAMPLE 31

E,E-3-Methyl-5-[2-1,1,3,3-tetramethyl-1,3-dihydro-5-isobenzofuranyl)-1-cyclopent-1-yl]-2,4-pentadienoic Acid Following the procedure of Examples 1 and 2, the title compound is prepared using the product from Example 25 and ethyl trifluoromethanesulfonyloxycyclopent- 1-yl carboxylate to give the desired product as colorless crystals.

mp=211–212° C. $^1$HNMR (CDCl$_3$): δ 1.47 (s, 6H), 1.54 (s, 6H), 1.98–2.03 (m, 2H), 2.27 (s, 3H), 2.71–2.76 (m, 2H), 2.85–2.92 (m, 2H), 5.85 (s, 1H), 6.30 (d, J=16.0 Hz, 1H), 7.02 (s, 1H), 7.08 (d, J=16.0 Hz, 1H), 7.11 (d, J=16.0 Hz, 1H), 7.23 (d, J=16.0 Hz, 1H). MS (CI): m/z 353 (M$^+$+H)

EXAMPLE 32

E,E-3-Methyl-5-[2-(1,1,3,3,6-pentamethyl-1,3-dihydro-5-isobenzofuranyl)-1-cyclopent-1-yl]-2,4-pentaidenoic Acid The reaction of 5-bromo-1,1,3,3,6-pentamethyl-1,3-dihydro-5-isobenzofuran as in Example 31 gives the desired compound as colorless crystals.

$^1$HNMR (CDCl$_3$) δ 1.49 (s, 6H), 1.53 (s, 6H), 2.02–2.07 (m, 2H), 2.16 (s, 3H), 2.21 (s, 3H), 2.67–2.78 (m, 4H), 5.80 (s, 1H), 6.22 (d, J=16.0 Hz, 1H), 6.58 (d, J=16.0 Hz, 1H), 6.76 (s, 1H), 6.92 (s, 1H).

EXAMPLE 33

E,E-3-Methyl-5-[2-(2-(3,5,5,8,8-pentamethyl-5,6,7,8-tetrahydro-2-naphthalenyl)-1-cyclopenten-1-yl]-2,4-pentadienol The product from Example 7 is reduced with lithium aluminum hydride in diethyl ether. The reaction mixture is quenched with water and the resultant mixture is extracted with ether, and on evaporation the desired compound is obtained.

EXAMPLES 34–41

The product of the indicated Example is reduced as in Example 33 to the corresponding alcohol as outlined in Table 5:

TABLE 5

| Example No. | Product of Example | Name of Product |
|---|---|---|
| 34 | 2 | E,E-3-Methyl-5-[2-(5,6,7,8-tetrahydro-5,5,8,8-tetramethyl-2-naphthalenyl)-1-cyclohexen-1-yl]-2,4-pentadienol |
| 35 | 6 | E,E-3-Methyl-5-[2-(5,6,7,8-tetrahydro-3,5,5,8,8-pentamethyl-2-naphthalenyl)-1-cyclohexen-1-yl]-2,4-pentadienol |
| 36 | 4 | E,E-3-Methyl-5-[2-(5,6,7,8-tetrahydro-5,5,8,8-tetramethyl-2-naphthalenyl)-1-cyclopenten-1-yl]-2,4-pentadienol |
| 37 | 8 | E,E-3-Methyl-5-[2-(5,6,7,8-tetrahydro-3,5,5,8,8-pentamethyl-2-naphthalenyl)-1-cyclopenten-1-yl]-2,4-pentadienol |
| 38 | 29 | E,E-3-Methyl-5-[2-(5,6,7,8-tetrahydro-3,5,5,8,8 pentamethyl-2-naphthalenyl)phenyl]-2,4-pentadienol |
| 39 | 30 | E,E-3-Methyl-5-[2-(5,6,7,8-tetrahydro-5,5,8,8-tetramethyl-2-naphthalenyl)phenyl]-2,4-pentadienol |
| 40 | 31 | E,E-3-Methyl-5-[2-(1,3-dihydro-1,1,3,3-tetramethyl-5-isobenzofuranyl)-1-cyclopent-1-yl]-2,4-pentadienol |
| 41 | 32 | E,E-3-Methyl-5-[2-(1,3-dihydro-1,1,3,3,6-pentamethyl-5-isobenzofuranyl)-1-cyclopent-1-yl]-2,4-pentadienol |

EXAMPLE 42

Z,E and E,E-3-Methyl-5-[2-(4-methoxy-2,3,6-trimethylphenyl)-1-cyclohexen-1-yl]-2 4-pentadienoic Acid Ethyl Ester To a stirred solution of 1-bromo-4-methoxy-2,3,6-trimethylbenzene in anhydrous tetrahydrofuran at −78° C. is added 1.7M tert-butyllithium in pentane, followed by the addition of zinc chloride, 0.5M in tetrahydrofuran. The mixture is allowed to warm to room temperature, tetrakis (triphenylphosphine) palladium(0) and ethyl 2-trifluoromethanesulfonyloxycyclohexen-1-ylcarboxylate in tetrahydrofuran is added and the resulting solution is stirred for 2 hours at the reflux temperature of the solvent. The reaction is cooled to room temperature, 50 ml of diethyl ether is added and the layers are separated. The organic layer is washed with water, aqueous sodium bicarbonate, saturated sodium chloride, and dried over sodium sulfate. Evaporation of the solution, followed by chromatography (silica gel: hexane/diethyl ether 4:1) gives 2-(4-methoxy-2, 3,6-trimethylphenyl)-1-cyclohexene-1-carboxylic acid, ethyl ester.

A solution of the above isolated solid in diethyl ether is added dropwise at 0° C. to 1.0N lithium aluminum hydride in anhydrous tetrahydrofuran, followed by stirring at room temperature for 15 minutes. Water is added dropwise to the cooled reaction mixture. The reaction is extracted with diethyl ether. The organic layers are combined, dried over sodium sulfate and evaporated to give the alcohol as an oil. The oil is dissolved in methyl alcohol to which is added triphenylphosphine hydrobromide and the reaction mixture is stirred at room temperature for 17 hours. The solvent is removed in vacuo, and the residue is washed with diethyl ether to give the corresponding phosphonium bromide which is then dissolved in dry methylene chloride, cooled under argon to 0° C., and sodium ethoxide and ethyl 3-methyl-4-oxocrotonate is added. The mixture is stirred at 0° C. for 1 hour and quenched with water. The methylene chloride extract is dried over sodium sulfate, evaporated and the residue is purified by chromatography (silica gel: hexane/diethyl ether 9:1) to give a mixture of E,E and Z,E esters.

EXAMPLE 43

E,E-3-Methyl-5- [2-(4-methoxy-2,3,6-trimethylphenyl)-1-cyclohexen-1-yl]-2,4-pentadienoic Acid The mixed ester product from Example 42 is combined with 2N aqueous potassium hydroxide in methyl alcohol and stirred at reflux temperature for 3 hours. The reaction mixture is cooled to room temperature, poured into a mixture of ice and methylene chloride, and acidified to pH 3 with 3N hydrochloric acid. The organic layers are combined, dried over sodium sulfate and evaporated to give a residue. The solid is recrystallized form absolute ethyl alcohol to give the desired compound.

EXAMPLE 44

E,E-3-Methyl-5-[2-(1,1,3,3,6-pentamethyl-1,3-dihydro-5-isobenzofuranyl)-1-cyclopent-1-yl]-2 4-pentadienoic Acid Using the procedure of Example 31 and substituting 5-bromo-1,1,3,3,6-pentamethylisobenzofuran, there is obtained the title compound.

EXAMPLE 45

E,E-3-Methyl-5-[2-(1,1,3,3,6-pentamethyl-1,3-dihydro-5-isobenzofuranyl)-1-cyclohexen-1-yl]-2,4-pentadienoic Acid Using the procedure of Example 27 and substituting 5-bromo-1,1,3,3,6-pentamethylisobenzofuran, there is obtained the title compound.

$^1$HNMR (CDCl$_3$) δ 1.47 (s, 3H), 1.50 (s, 3H), 1.52 (s, 6H), 1.70–1.86 (m, 4H), 1.98 (s, 3H), 2.16 (s, 3H), 2.29–2.39 (m, 4H), 5.75 (s, 1H), 6.21 (d, J=16.0 Hz, 1H), 6.41 (d, J=16.0 Hz, 1H), 6.72 (s, 1H), 6.91 (s, 1H).

EXAMPLE 46

Z,E and E,E-3-Trifluoromethyl-5-[2-(5,6,7,8-tetrahydro-5,5,8,8-tetramethyl-2-naphthalenyl)-1-cyclohexen-1-yl]-2,4-pentadienoic Acid Methyl Ester Ethyl 2-(5,6,7,8-tetrahydro-5,5,8,8-tetramethyl-2-naphthalenyl)-1-cyclohexene-1-carboxylate, described in Example 1, is stirred with excess lithium aluminum hydride in diethyl ether at reflux temperature for 3 hours. The mixture is cooled and water is added dropwise. The organic layer is dried over sodium sulfate and evaporated to give 2-(5,6,7,8-tetrahydro-5,5,8,8-tetramethyl-2-naphthalenyl)-1-cyclohexenylmethanol.

The above alcohol is stirred with excess manganese dioxide in methylene chloride for 5 hours. The reaction mixture is dried over sodium sulfate, filtered, and evaporated to give 2-(5,6,7,8-tetrahydro-5,5,8,8-tetramethyl-2-naphthalenyl)-1-cyclohexene carboxaldehyde.

To one equivalent of lithium diisopropylamide in tetrahydrofuran/hexamethylphosphoramide (2:1) is added one equivalent of methyl β-trifluoromethy-γ-diethylphosphono-methacrylate, dropwise, at 0° C. The reaction mixture is stirred at room temperature for 45 minutes, then cooled to 0° C. and one equivalent of the above aldehyde dissolved in dry tetrahydrofuran is added. The reaction mixture is stirred at room temperature for 24 hours. Water is added and the mixture is extracted with diethyl ether. The organic layer is dried over sodium sulfate, filtered and evaporated to give the titled compound as a mixture of isomers.

EXAMPLE 47

E,E-3-Trifluoromethyl-5-[5,6,7,8-tetrahydro-5,5,8,8-tetramethyl-2-naphthalenyl)-1-cyclohexen-1-yl]-2,4-pentadienoic Acid The mixed ester product from Example 46 is combined with 2N aqueous potassium hydroxide in methyl alcohol. The reaction mixture is stirred at reflux temperature for 3 hours, cooled to room temperature, poured into a mixture of ice and methylene chloride, and acidified to pH 3.0 with 3N hydrochloric acid. The organic layers are combined, dried over sodium sulfate and evaporated to give a residue. The crude product is recrystallized from absolute ethyl alcohol to give the desired compound as crystals.

EXAMPLE 48

Ethyl 2-Trifluoromethanesulfonyloxycycloheptenecarboxylate

A solution of one equivalent of ethyl 2-cycloheptanonecarboxylate and one equivalent of diisopropylamine in methylene chloride is cooled to 0° C., and one equivalent of trifluoromethanesulfonic anhydride is added, dropwise. The reaction mixture is stirred for 5 hours at room temperature, filtered through course silica gel, concentrated in vacuo, and the residue is distilled under reduced pressure to give the desired product.

EXAMPLE 49–55

The indicated substrate is reacted as in Example 48 to give the corresponding enol triflate as outlined in Table 6.

TABLE 6

| Example No. | Substrate | Product |
|---|---|---|
| 49 | Methyl tetrahydro-4-oxo-3-thiophenecarboxylate | CH₃O₂C—[thiophene]—OTf |
| 50 | Ethyl tetrahydrofuran-4-one-3-carboxylate | C₂H₅O₂C—[furan]—OTf |
| 51 | Methyl 4-hydroxythiophene-2-carboxylate | CH₃O₂C—[thiophene]—OTf |
| 52 | Methyl tetrahydro-3-oxo-2-thiophenecarboxylate | [thiophene with CO₂CH₃ and OTf] |
| 53 | Methyl tetrahydropyran-4-one-3-carboxylate | [pyran with CO₂CH₃ and OTf] |
| 54 | Ethyl tetrahydrothiopyran-4-one-3-carboxylate | [thiopyran with CO₂C₂H₅ and OTf] |

EXAMPLE 55–61

The indicated substrate is reacted in a manner essentially equivalent to that of Example 5 and 6 to give the corresponding product as outlined in Table 7.

TABLE 7

| Example No. | Substrate | Product |
|---|---|---|
| 55 | CH₃O₂C—[thiophene]—OTf | E,E-5-[2,5-Dihydro-4-(5,6,7,8-tetrahydro-3,5,5,8,8-pentamethyl-2-naphthalenyl)-3-thienyl]-3-methyl-2,4-pentadienoic Acid |
| 56 | C₂H₅O₂C—[furan]—OTf | E,E-5-[2,5-Dihydro-4-5,6,7,8-tetrahydro-3,5,5,8,8-pentamethyl-2-naphthalenyl)-3-furanyl]-3-methyl-2,4-pentadienoic Acid |

TABLE 7-continued

| Example No. | Substrate | Product |
|---|---|---|
| 57 | CH₃O₂C—[thiophene]—OTf | E,E-5-[4-(5,6,7,8-Tetrahydro-3,5,5,8,8-pentamethyl-2-naphthalenyl)-3-thienyl]-3-methyl-2,4-pentadienoic Acid |
| 58 | [thiophene with CO₂CH₃ and OTf] | E,E-5-[4,5-Dihydro-3-(5,6,7,8-tetrahydro-3,5,5,8,8-pentamethyl-2-naphthalenyl)-2-thienyl]-3-methyl-2,4-pentadienoic Acid |
| 59 | TfO—[pyran]—CO₂CH₃ | E,E-5-[5,6-Dihydro-4-(5,6,7,8-tetrahydro-3,5,5,8,8-pentamethyl-2-naphthalenyl)-2-$\underline{H}$-pyranyl-3-yl]-3-methyl-2,4-pentadienoic Acid |
| 60 | CH₃O₂C—[pyran]—OTf | E,E-5-[3,6-Dihydro-5-(5,6,7,8-tetrahydro-3,5,5,8,8-pentamethyl-2-naphthalenyl)-2-$\underline{H}$-pyranyl-4-yl]-3-methyl-2,4-pentadienoic Acid |
| 61 | TfO—[thiopyran]—CO₂C₂H₅ | E,E-5-[5,6-Dihydro-4-(5,6,7,8-tetrahydro-3,5,5,8,8-pentamethyl-2-naphthalenyl)-2-$\underline{H}$-thiopyranyl-3-yl]-3-methyl-2,4-pentadienoic Acid |

EXAMPLE 62

E,E-3-Methyl-5-[2-(3-methoxy-5,6,7,8-tetrahydro-5,5,8,8-tetramethyl-2-naphthalenyl)-1-cyclohexen-1-yl]-2,4-pentadienoic Acid The reaction of o-bromoanisole with 2,3-dichloro-2,3-dimethyl butane as described in P. Loeliger et al, *Eur. J. Med. Chem.-Chim. Ther*, 1980, 15, 9–15 gives 2-bromo-3-methoxy-5,6,7,8-tetrahydro-5,5,8,8-tetramethylnaphthalene, which is then reacted in a manner analogous to Examples 1 and 2 to give the title compound.

EXAMPLE 63

E,E-3-Methyl-5-[2-(5,6,7,8-tetrahydro-5,5,8,8-tetramethyl-3-trifluoromethyl-2-naphthalenyl)-1-cyclohexen-1-yl]-2,4-pentadienoic Acid A mixture of one equivalent of 2-bromo-3,5,5,8,8-pentamethyl-5,6,7,8-tetrahydronaphthalene and three equivalents of N-bromosuccinimide in carbon tetrachloride is irradiated with a 500 W tungsten lamp for 5 hours. The misture is cooled, filtered, and the solvent is removed in vacuo to give 2-bromo-5,6,7,8-tetrahydro-5,5,8,8-tetramethyl-3-tribromomethylnaphthalene, which is hydrolyzed with a mixture of aqueous potassium bicarbonate and acetone. The mixture is filtered and the acetone is removed in vacuo. The residue ia dissolved in water, acidified with dilute hydrochloric acid to give 3-bromo-5,6,7,8-tetrahydro-5,5,8,8-tetramethyl-2-naphthoic acid. Reacting this acid with SF₄ and hydrogen flouride according to the procedure of B. V. Kunshenko, *J. Org. Chem. USSR* (English translation), 10, 8996 (1974) gives 2-bromo-5,6,7,8- tetrahydro-5,5,8,8-tetramethyl-3-trifluoromethylnaphthalene, and this is reacted as in Example 1 and 2 to give the title compound.

EXAMPLE 64

E,E-3-Methyl-5-[2-(2-(3,5,5,8,8-pentamethyl-5,6,7,8-tetrahydro-2-naphthalenyl)-1-cyclopenten-1-yl]-2,4-pentadienoic Acid Methyl Ester The compound of Example 8 is reacted with trimethylsilyl diazomethane in benzene-methanol (7:3) for 10 minutes at room temperature to give the title compound in quantitative yield.

m.p.=170–173° C. $^1$HNMR (300 MHz, CDCl$_3$): δ 1.25 (s, 6H), 1.30 (s, 6H), 1.68 (s, 4H), 2.02 (pent, J=6.9 Hz, 2H), 2.17 (s, 3H), 2.18 (s, 3H), 2.63–2.71 (m, 2H), 2.73–2.82 (m, 2H), 3.69 (s, 3H), 5.78 (s, 1H), 6.20 (d, J=15.8 Hz, 1H), 6.65 (d, J=15.8 Hz, 1H), 6.96 (s, 1H), 7.11 (s, 1H).

EXAMPLE 65

E,E-5-[2-(5,6,7,8-Tetrahydro-3,5,5,8,8-pentamethyl-2-naphthalenyl)-2-thienyl]-3-methyl-2,4-pentadienoic Acid Methyl Ester A solution of 50 g of thiophene-3-carboxaldehyde, 40 ml of ethylene glycol, and 1.0 g of p-toluenesulfonic acid in 200 ml of benzene is refluxed with water removal for 6 hours. Evaporation of the solvent gives the corresponding ethylene ketal. A solution of 15.61 g of this ketal in 120 ml of tetrahydrofuran is reacted sequentially with 50 ml of 2.5 M n-butyllithium in hexane at −78° C. under argon then 31 ml of triisopropyl borate at 0° C. To this is added 34.0 g of 2-bromo-5,6,7,8-tetrahydro-3,5,5,8,8-pentamethylnaphthalene and 3.5 g of tetrakistriphenylphosphinepalladium (O), and this is refluxed under argon for 8 hours to give the corresponding 2-aryl-3-thiophenecarboxaldehyde ethylene ketal. This is hydrolyzed in acetone-water-p-toluenesulfonic acid to give the corresponding aldehyde. Reaction of 1.3 g of the above aldehyde with the ylide prepared from 1.6 g of methyl 3-methyl-4-dimethylphosphorylcrotonate and 0.3 g of sodium hydride in 30 ml of tetrahydrofuran and 10 ml of hexamethylphosphoramide gives the title compound m.p.=152–153° C. $^1$HNMR (CDCl$_3$): δ 1.26 (s, 6H), 1.32 (s, 6H), 1.70 (s, 6H), 2.19 (s, 3H), 2.22 (s, 3H), 3.70 (s, 3H), 5.82 (s, 1H), 6.62 (d, J=16.0 Hz, 1H), 6.68 (d, J=16.0 Hz, 1H), 7.15 (s, 1H), 7.19 (s, 1H), 7.29 (d, J=6.0 Hz, 1H), 7.33 (d, J=6.0 Hz, 1H) ppm.

EXAMPLE 66

E,E-5-[2-(5,6,7,8-Tetrahydro-3,5,5,8,8-pentamethyl-2-naphthalenyl)-3-thienyl]-3-methyl-2,4-pentadienoic Acid Hydrolysis of the title compound of Example 65 with 3N potassium hydroxide, followed by acidification with 3N hydrochloric acid gives the above title compound. m.p.= 194–195° C.

$^1$HNMR (CDCl$_3$): δ 1.26 (s, 6H), 1.32 (s, 6H), 1.70 (s, 6H), 2.20 (s, 3H), 2.23 (s, 3H), 5.84 (s, 1H), 6.63 (d, J=16.0 Hz, 1H), 6.73 (d, J=16.0 Hz, 1H), 7.15 (s, 1H), 7.20 (s, 1H), 7.29 (d, J=6.0 Hz, 1H), 7.34 (d, J=6.0 Hz, 1H) ppm.

EXAMPLE 67

E,E-5-[3-(5,6,7,8-Tetrahydro-3,5,5,8,8-pentamethyl-2-naphthalenyl)-2-thienyl]-3-methyl-2,4-pentadienoic Acid To a mixture of 17.0 g of 2-bromo-5,6,7,8-tetrahydro-3,5,5,8,8-pentamethylnaphthalene in 60 ml of tetrahydrofuran at −78° C. under argon is added one equivalent of t-butyllithium in pentane and this is stirred for 30 minutes, followed by stirring at room temperature for one hour. The mixture is then cooled to −78° C. and 20 ml of triisopropylborate is added and this is stirred for one hour followed by stirring for 2 hours at room temperature. Workup with hydrochloric acid gives the corresponding boronic acid as a pesquihydrate. A solution of 3.0 g of methyl 3-bromothiophenecarboxylate in 14 ml dimethoxyethane with tetrakistriphenylphosphinepalladium (O), followed by the above boronic acid in ethanol and then 50 ml of saturated sodium bicarbonate is refluxed under argon for 3 hours. Aqueous workup gives methyl 3-(5,6,7,8-tetrahydro-3,5,5,8,8-pentamethyl-2-naphthyl)thiophene-2-carboxylate, m.p. 89–90° C.

Reduction of this ester with excess lithium aluminum hydride, followed by acidation of the resulting alcohol with manganese dioxide gives the corresponding aldehyde. This aldehyde is reacted in a manner similar to Example 65 with the ylide generated from methyl 3-methyl-4-dimethylphosphonylcrotonate to give the title compound as the methyl ester. Hydrolysis with 2 N KOH followed by acidification with 3 N HCl gives the title compound. m.p.= 208–209° C.

$^1$HNMR (CDCl$_3$): δ 1.26 (s, 6H), 1.32 (s, 6H), 1.70 (s, 4H), 2.17 (s, 3H), 2.22 (s, 3H), 5.85 (s, 1H), 6.65 (d, J=16.0 Hz, 1H), 6.93 (d, J=16.0 Hz, 1H), 7.01 (d, J=5.0 Hz, 1H), 7.07 (s, 1H), 7.20 (s, 1H), 7.25 (d, J=5.0 Hz, 1H) ppm.

EXAMPLE 68

(Z,E)-5-[3-[2-(5,6,7,8-tetrahydro-3,5,5,8,8-pentamethyl-2-naphthalenyl)-1-cyclohexen-yl]-2-propenylidene-2,4-thiazolidinedione To 1.36 mL (1.53 g, 8.38 mmol) of trimethyl phosphonoacetate in 30 mL tetrahydrofuran is added 89 mg (0.34 mmol) of 18-crown-6. This solution is cooled to 0° C. and 6.70 mL (3.35 mmol) of a 0.5 M solution of potassium hexamethyldisilazane/toluene is added in drops. After stirring at 0° C. for 30 min, 520 mg of 2-(3,5,5,8,8-pentamethyl-5,6,7,8-tetrahydronaphth-2-yl)cyclohexen-1-carboxaldehyde in 10 mL tetrahydrofuran is added in drops via cannula, and the resulting mixture is stirred at 23° C. for 65 hours. After quenching with 10 mL of saturated aqueous NH$_4$Cl, the reaction mixture is poured into 50 mL of brine and extracted with 3×50 mL of ether. The combined organics are washed with 2×50 mL of brine, dried over MgSO$_4$, filtered and evaporated to a colorless oil. Flash chromatography on silica gel, eluting with hexanes/CH$_2$Cl$_2$ (2/1 to 1/1), gives 578 mg (1.58 mmol, a 94% yield) of methyl E-3-(3,5,5,8,8-pentamethyl-5,6,7,8-tetrahydronaphth-2-yl) acrylate as a colorless oil:

$^1$H NMR (300 MHz, CDCl$_3$): d 1.24 (s, 6H), 1.28 (s, 3H), 1.30 (s, 3H), 1.67 (s, 4H), 1.70–1.84 (m, 4H), 2.07 (s, 3H), 2.10–2.37 (m, 4H), 3.65 (s, 3H), 5.80 (d, J=15.8 Hz, 1H), 6.86 (s, 1H), 7.07 (s, 1H), 7.18 (d, J=15.8 Hz, 1H); $^{13}$C NMR (75 MHz, CDCl$_3$): d 19.1, 22.5, 22.7, 25.0, 31.9, 32.0, 32.1, 33.6, 33.9, 34.0, 35.4, 51.1, 114.7, 126.5, 127.9, 129.7, 131.7, 138.6, 142.1, 143.7, 145.1, 148.7, 168.1; IR (Nujol, cm$^{-1}$): 3015m, 2926s, 2859s, 1723s, 1617m, 1496m, 1455m, 1434s, 1307s, 1295s, 1273s, 1189m, 1133s, 1071m, 987m, 856m; MS (EI) m/z (relative intensity): 366 (M$^+$, 100), 351 (M$^+$—CH$_3$, 75), 319 (60), 295 (25), 281 (45), 241 (45), 165 (25), 111 (100); HRMS (EI) calcd for C$_{25}$H$_{34}$O$_2$: 366.2559; found 366.2549; Anal. calcd for C$_{25}$H$_{34}$O$_2$: C, 81.92, H, 9.35. Found: C, 82.19, H, 9.39, in addition to 18 mg (0.05 mmol, a 2% yield) of the Z isomer as a light yellow oil: $^1$H NMR (300 MHz, CDCl$_3$): d 1.20 (s, 3H), 1.24 (s, 3H), 1.26 (s, 6H), 1.65 (s, 4H), 1.68–1.80 (m, 4H), 2.09 (s, 3H), 2.08–2.34 (m, 4H), 3.72 (s, 3H), 5.44 (d, J=12.7 Hz, 1H), 6.23 (d, J=12.7 Hz, 1H), 6.87 (s, 1H), 7.03 (s, 1H); IR (Nujol, cm$^{-1}$): 3017m, 2957s, 2859s, 1724s, 1618m, 1496m, 1457m, 1437m, 1363w, 1227–1171brs, 758s; MS (EI) m/z (relative intensity): 366 (M$^+$, 100), 351 (M$^+$—CH$_3$, 75), 319 (60), 281 (50), 241 (40), 111 (100).

To 470 mg (1.28 mmol) of the above ester in 25 mL of CH$_2$Cl$_2$ at –78 ° C. is added 2.82 mL (2.82 mmol) of a 1.0 M solution of Dibal/hexanes. After 30 min at –78° C. an additional 1.0 mL (1.00 mmol) of 1.0 M Dibal/hexanes is added. The reaction mixture is quenched with 10 mL of saturated aqueous solution potassium sodium tartrate and warmed to 23° C. with stirring for 30 min. The resulting mixture is poured into 50 mL of 1 N NaOH, extracted with 3×50 mL of Et$_2$O, and the combined organics are washed with 1×100 mL of H$_2$O, 1×100 mL of brine, dried over Na$_2$SO$_4$, filtered and evaporated to give a colorless oil. Flash chromatography on silica gel, eluting with hexanes/EtOAc (8/1 to 4/1) gives 430 mg (1.27 mmol, a 99% yield) of E-3-(3,5,5,8,8-pentamethyl-5,6,7,8-tetrahydronaphth-2-yl)-2-propen-1-ol as an oily white solid . R$_f$=0.21 (8/1 hexanes/EtOAc); $^1$H NMR (300 MHz, CDCl$_3$): d 1.23 (s, 3H), 1.24 (s, 3H), 1.28 (s, 3H), 1.29 (s, 3H), 1.67 (s, 4H), 1.65–1.82 (brm, 4H), 2.07 (s, 3H), 2.10–2.37 (m, 5H), 4.04 (t, J=6.3 Hz, 2H), 5.74 (dt, J=15.8, 9.1 Hz, 1H), 6.03 (d, J=15.8 Hz, 1H), 6.89 (s, 1H), 7.05 (s, 3H); $^{13}$C NMR (75 MHz, CDCl$_3$): d 19.0, 22.9, 23.1, 25.2, 31.9, 32.0, 32.1, 33.0, 33.9, 35.4, 64.3, 124.9, 126.5, 127.6, 129.5, 132.0, 132.5, 139.7, 140.1, 142.0, 143.0; IR (KBr, cm$^{-1}$): 3467brm, 3033w, 3014w, 2961s, 2927s, 2855s, 2835m, 1641w, 1495m, 1457brm, 1389w, 1361w, 1234w, 1110w, 1035w, 1010m, 973w, 894w; MS (EI) m/z (relative intensity): 339 (M$^+$, 50), 323 (M$^+$—CH$_3$, 20), 305 (30), 293 (50), 237 (35), 223 (25), 111 (100); Anal. calcd for: C, 85.15, H, 10.12. Found: C, 84.27, H, 10.29.

To 570 mg (1.34 mmol) of Dess-Martin periodinane in 25 mL CH$_2$Cl$_2$ at 23° C. is added a solution of 364 mg (1.08 mmol) of the above alcohol in 10 mL CH$_2$Cl$_2$ in drops via a cannula. After stirring at 23° C. for 1.5 h, the reaction mixture is poured into 50 mL saturated aqueous NaHCO$_3$ containing 5 g Na$_2$S$_2$O$_3$ and stirred vigorously until the layers clear. The organic layer is separated and the remaining aqueous mixture is extracted with 2×25 mL CH$_2$Cl$_2$, the organics are combined, dried over MgSO$_4$, filtered and evaporated to give a colorless oil. Flash chromatography on silica gel, eluting with hexanes/EtOAc (8/1) gives 276 mg (0.82 mmol, a 76% yield) of E-3-(3,5,5,8,8-pentamethyl-5, 6,7,8-tetrahydronaphth-2-yl)propenal as a colorless oil. R$_f$=0.48 (8/1 hexanes/EtOAc); $^1$H NMR (300 MHz, CDCl$_3$): d 1.23, (s, 3H), 1.26 (s, 3H), 1.29 (s, 3H), 1.31 (s, 3H), 1.68 (s, 4H). 1.71–1.83 (brm, 4H), 2.09 (s, 3H), 2.22–2.40 (m, 4H), 6.09 (dd, J=8.0, 15.7 Hz, 1H), 6.88 (s, 1H), 6.95 (d, J=15.7 Hz, 1H), 7.10 (s, 1H), 9.31 (d, J=8.0 Hz, 1H); $^{13}$C NMR (75 MHz, CDCl$_3$): d 19.0, 22.4, 22.6, 25.0, 31.8, 31.9, 32.0, 33.8, 34.0, 35.2, 126.3, 126.4, 128.1, 130.4, 131.6, 138.3, 142.4, 144.5, 151.4, 152.8, 190.3; R (Nujol, cm$^1$): 3016w, 2958s, 2928s, 2863m, 1680s, 1609m, 1496w, 1457m, 1363w, 1274–973brm, 756w; MS (EI) m/z (relative intensity): 336 (M$^+$, 100), 321 (M$^+$—3, 75), 307 (45), 295 (50), 229 (75), 111 (70); HRMS (EI) calcd for C$_{24}$H$_{32}$O: 336.2453; found 336.2457.

To 238 mg (0.71 mmol) of the above aldehyde is added 20 mL of toluene, 99 mg (0.85 mmol) of 2,4 thiazolinedione, 40 ml (30 mg, 0.35 mmol) of piperidine, 20 ml (21 mg, 0.35 mmol) of glacial acetic acid, and 1 g of activated powdered 4 Å molecular sieves. After heating at 80 ° C. for 2 h, the resulting yellow slurry is filtered through a 1" pad of Celite, the resulting filtrate is diluted with 100 mL of Et$_2$O, extracted with 1×50 mL of saturated aqueous NaHCO$_3$, 1×50 mL of brine, dried over MgSO$_4$, filtered and evaporated to a yellow oil. Flash chromatography on silica gel, eluting with petroleum ether/EtOAc (8/1 to 4/1) gives 138 mg (0.32 mmol, a 45% yield) of the title compound as a yellow solid. R$_f$=0.42 (2/1 hexanes/EtOAc); $^1$H NMR (300 MHz, CDCl$_3$): d 1.24 (s, 6H), 1.29 (s, 3H), 1.33 (s, 3H), 1.69 (s, 4H), 1.76–1.85 (brm, 4H), 2.05 (s, 3H), 2.31–2.40 (brm, 4H), 6.00 (dd, J=11.5, 15.0 Hz, 1H), 6.04 (d, J=15.0 Hz, 1H), 6.85 (s, 1H), 7.09 (s, 1H), 7.26 (s, 1H), 8.10 (brs, 1H); $^{13}$C NMR (75 MHz, CDCl$_3$): d 19.0, 22.5, 22.6, 24.9, 32.0, 32.1, 33.8, 34.0, 34.1, 35.3, 119.8, 121.0, 126.1, 127.8, 131.0, 131.7, 135.6, 138.6, 142.4, 144.0, 145.7, 149.1, 165.6, 166.5; IR (KBr, cm$^{-1}$): 3330brw, 3262brw, 3015w, 2958m, 2927m, 2860w, 1741m, 1688s, 1588m, 1496w, 1456w, 1390w, 1362m, 1331m, 1169w, 1145w, 970vw; MS (EI) m/z (relative intensity): 435 (M$^+$, 100), 420 (M$^+$—CH$_3$, 20), 366 (45), 278 (25), 111 (5); HRMS (EI) calcd for C$_{27}$H$_{33}$NO$_2$S: 435.2232; found 435.2232.

We claim:

1. A compound of Formula I:

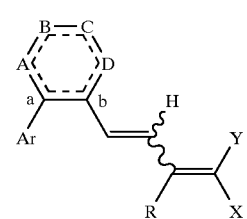

Formula I wherein:

A, B and C are CH, CH$_2$, O, or S wherein no more than one heteroatom is present;

D is (CH)$_m$, and m is an integer 0 to 1; or D is (CH$_2$)$_n$, and n is an integer 0 to 2;

the dotted line, -----, represents the presence or absence of a double bond whereby if only one double bond is present, it is disposed to the a-b position; or if multiple double bonds are present they are in a conjugated position to produce an aromatic ring;

R is hydrogen, methyl, ethyl, t-butyl, or trifluoromethyl;

Ar is:

a moiety of the formula:

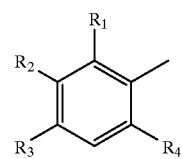

wherein R$_1$, R$_2$, R$_3$, and R$_4$ are hydrogen, (C$_1$–C$_3$) alkyl, (C$_1$–C$_3$)alkoxy or trifluoromethyl;

a moiety of the formula:

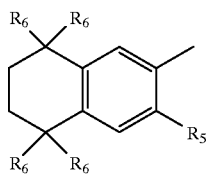

wherein $R_5$ is hydrogen, $(C_1-C_3)$alkyl, methoxy or trifluoromethyl;
$R_6$ is hydrogen, methyl or ethyl;
or a moiety of the formula:

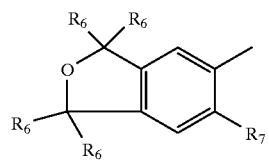

wherein $R_6$ is hydrogen, methyl or ethyl;
$R_7$ is hydrogen, methyl or ethyl; Y is hydrogen, and X is $CH_2OH$, CHO, $CO_2H$, CN, $CH_2CONH_2$, or a moiety of the formula:

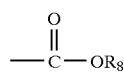

and $R_8$ is straight or branched $(C_1-C_8)$alkyl, or

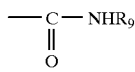

wherein $R_9$ is hydrogen, straight or branched $(C_1-C_{10})$ alkyl, glycosyl, 2-methoxyethyl, 2-dimethylaminoethyl, (1,2 or 3)-pyridyl, or (1,2 or 3)-pyridylmethyl; or X and Y taken together form the thiazolidinedione ring of the formula:

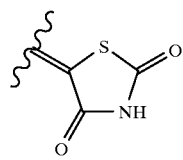

and the pharmaceutically acceptable salts and esters.

2. A compound of Formula I:

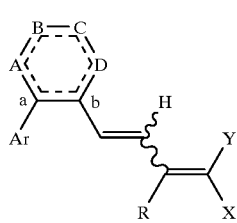

Formula I wherein:
A, B and C are CH, $CH_2$, O, or S wherein no more than one heteroatom is present;

D is $(CH)_m$, and m is an integer 0 to 1; or D is $(CH_2)_n$, and n is an integer 0 to 2;

the dotted line, -----, represents the presence or absence of a double bond whereby if only one double bond is present, it is disposed to the a-b position; or if multiple double bonds are present they are in a conjugated position to produce an aromatic ring;

R is hydrogen, methyl, ethyl, t-butyl, or trifluoromethyl;

Ar is:
a moiety of the formula:

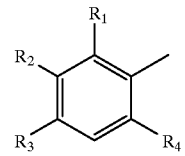

wherein $R_1$, $R_2$, $R_3$, and $R_4$ are hydrogen, $(C_1-C_3)$ alkyl, $(C_1-C_3)$alkoxy or trifluoromethyl; and X is $CH_2OH$, CHO, $CO_2H$, CN, $CH_2CONH_2$, or a moiety of the formula:

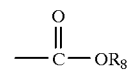

and $R_8$ is straight or branched $(C_1-C_8)$alkyl, or

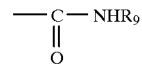

wherein $R_9$ is hydrogen, straight or branched $(C_1-C_{10})$ alkyl, glycosyl, 2-methoxyethyl, 2-dimethylaminoethyl, (1,2 or 3)-pyridyl, or (1,2 or 3)-pyridylmethyl; Y is hydrogen, and the pharmaceutically acceptable salts and esters.

3. A compound of Formula I:

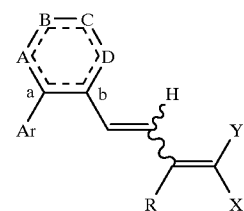

Formula I wherein:
A is CH or $CH_2$;
B and C are CH, $CH_2$, O, or S wherein no more than one heteroatom is present;

D is $(CH)_m$, and m is an integer 0 to 1; or D is $(CH_2)_n$, and n is an integer 0 to 2;

the dotted line, -----, represents the presence or absence of a double bond whereby if only one double bond is present, it is disposed to the a-b position; or if multiple double bonds are present they are in a conjugated position to produce an aromatic ring;

R is hydrogen, methyl, ethyl, t-butyl, or trifluoromethyl;

Ar is:

a moiety of the formula:

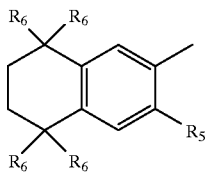

wherein $R_5$ is hydrogen, $(C_1-C_3)$alkyl, methoxy or trifluoromethyl;

$R_6$ is hydrogen, methyl or ethyl, and

X is $CH_2OH$, CHO, $CO_2H$, CN, $CH_2CONH_2$, or a moiety of the formula:

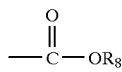

and $R_8$ is straight or branched $(C_1-C_8)$alkyl, or

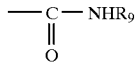

wherein $R_9$ is hydrogen, straight or branched $(C_1-C_{10})$ alkyl, glycosyl, 2-methoxyethyl, 2-dimethylaminoethyl, (1,2 or 3)-pyridyl, or (1,2 or 3)-pyridylmethyl; Y is hydrogen, and the pharmaceutically acceptable salts and esters.

4. A compound of Formula I:

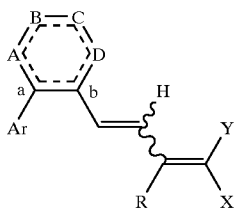

Formula I wherein:

A is CH or $CH_2$;

B and C are CH, $CH_2$, O, or S wherein no more than one heteroatom is present;

D is $(CH)_m$, and m is an integer 0 to 1; or D is $(CH_2)_n$, and n is an integer 0 to 2;

the dotted line, -----, represents the presence or absence of a double bond whereby if only one double bond is present, it is disposed to the a-b position; or if multiple double bonds are present they are in a conjugated position to produce an aromatic ring;

R is hydrogen, methyl, ethyl, t-butyl, or trifluoromethyl;

Ar is:

a moiety of the formula:

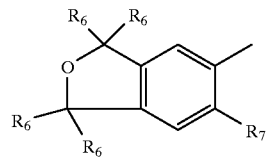

wherein $R_6$ is hydrogen, methyl or ethyl;

$R_7$ is hydrogen, methyl or ethyl; and

X is $CH_2OH$, CHO, $CO_2H$, CN, $CH_2CONH_2$, or a moiety of the formula:

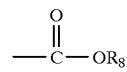

and $R_8$ is straight or branched $(C_1-C_8)$alkyl, or

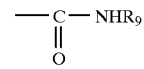

wherein $R_9$ is hydrogen, straight or branched $(C_1-C_{10})$ alkyl, glycosyl, 2-methoxyethyl, 2-dimethylaminoethyl, (1,2 or 3)-pyridyl, or (1,2 or 3)-pyridylmethyl; Y is hydrogen, and the pharmaceutically acceptable salts and esters.

5. A compound according to claim 3, Z,E and E,E-3-Methyl-5-[2-(5,6,7,8-tetrahydro-5,5,8,8-tetramethyl-2-naphthalenyl)-1-cyclohexen-1-yl]-2,4-pentadienoic Acid Ethyl Ester.

6. A compound according to claim 3, E,E-3-Methyl-5-[2-(5,6,7,8-tetrahydro-5,5,8,8-tetramethyl-2-naphthalenyl)-1-cyclohexen-1-yl]-2,4-pentadienoic Acid.

7. A compound according to claim 3, Z,E and E,E-3-Methyl-5-[2-(5,6,7,8-tetrahydro-5,5,8,8,-tetramethyl-2-naphthalenyl)-1-cyclopenten-1-yl]-2,4-pentadienoid Acid Ethyl Ester.

8. A compound according to claim 3, E,E-3-Methyl-5-[2-(5,6,7,8-tetrahydro-5,5,8,8-tetramethyl-2-naphthalenyl)-1-cyclopenten-1-yl]-2,4-pentadienoic Acid.

9. A compound according to claim 3, Z,E,- and E,E-3-Methy-5-[2-(3,5,5,8,8-pentamethyl-5,6,7,8,-tetrahydro-2-naphthalenyl)-1-cyclohexen-1-yl]-2,4-pentadienoic Acid Ethyl Ester.

10. A compound according to claim 3, E,E-3-Methyl-5-[2-(3,5,5,8,8-pentamethyl-5,6,7,8-tetrahydro-2-naphthalenyl)-1-cyclohexen-1-yl]-2,4-pentadienoic Acid.

11. A compound according to claim 3, Z,E- and E,E-3-Methyl-5-[2-(2-(3,5,5,8,8-pentamethyl-5,6,7,8-tetrahydro-2-naphthalenyl)-1-cyclopenten-1-yl]-2,4-pentadienoic Acid Ethyl Ester.

12. A compound according to claim 3, E,E-3-Methyl-5-[2-(3,5,5,8,8-pentamethyl-5,6,7,8-tetrahydro-2-naphthalenyl)-1-cyclopenten-1-yl-2,4-pentadienoic Acid.

13. A compound according to claim 3, 3-Methyl-5-[2-(5,6,7,8-tetrahydro-3,5,5,8,8-pentamethyl-2-naphthalenyl) phenyl]-2,4-pentadienoic Acid.

14. A compound according to claim 3, (Z, E)-5-[3-[2-(5,6,7,8-tetrahydro-3,5,5,8,8-pentamethyl-2-naphthalenyl)-1-cyclohexen-1-yl]-2-propenylidene]-2,4-thiazolidinedione.

15. A compound according to claim 3, 3-Methyl-5-[2-(5, 6,7,8-tetrahydro-5,5,8,8-tetramethyl-2-naphthalenyl) phenyl]-2,4-pentadienoic Acid.

16. A compound according to claim 4, E,E-3-Methyl-5-[2-(1,1,3,3-tetramethyl-1,3-dihydro-5-isobenzofuranyl)-1-cyclopent-1-yl]-2,4-pentadienoic Acid.

17. A method for the treatment of coronary artery disease in a mammal which comprises administering a therapeutically effective amount of a compound of claim 1.

18. A method of increasing plasma HDL levels in a mammal which comprises administering to said mammal a therapeutically effective amount of a compound of claim 1.

19. A method for the treatment of atherosclerosis in a mammal which comprises administering a therapeutically effective amount of a compound of claim 1.

20. A method according to claim 17 wherein said compound is E,E-3-Methyl-5-[2-(3,5,5,8,8-pentamethyl-5,6,7,8-tetrahydro-2-naphthalenyl)-1-cyclopenten-1yl-2,4-pentadienoic Acid.

21. A method according to claim 17 wherein said compound is E,E-3-Methyl-5-[2-(5,6,7,8-tetrahydro-5,5,8,8-tetramethyl-2-naphthalenyl)-1-cyclohexen-1-yl]-2,4-pentadienoic Acid.

22. A method according to claim 18 wherein said compound is E,E-3-Methyl-5-[2-(3,5,5,8,8-pentamethyl-5,6,7,8-tetrahydro-2-naphthalenyl)-1-cyclopenten-1yl-2,4-pentadienoic Acid.

23. A method according to claim 18 wherein said compound is E,E-3-Methyl-5-[2-(5,6,7,8-tetrahydro-5,5,8,8-tetramethyl-2-naphthalenyl)-1-cyclohexen-1-yl-2,4-pentadienoic Acid.

24. A method according to claim 19 wherein said compound is E,E-3-Methyl-5-[2-(3,5,5,8,8-pentamethyl-5,6,7,8-tetrahydro-2-naphthalenyl)-1-cyclopenten-1-yl]-2,4-pentadienoic Acid.

25. A method according to claim 19 wherein said compound is E,E-3-Methyl-5-[2-(5,6,7,8-tetrahydro-5,5,8,8-tetramethyl-2-naphthalenyl)-1-cyclohexen-1-yl]-2,4-pentadienoic Acid.

26. A method of treating cancers by induction of tumor cell differentiation in a mammal which comprises administering to said mammal a therapeutically effective amount of a compound of claim 1.

27. A compound according to claim 26, E,E-3-Methyl-5-[2-(5,6,7,8-tetrahydro-5,5,8,8-tetramethyl-2-naphthalenyl)-1-cyclohexen-1-yl]-2,4-pentadienoic Acid.

28. A compound according to claim 26, E,E-3-Methyl-5-[2-(5,6,7,8-tetrahydro-5,5,8,8-tetramethyl-2-naphthalenyl)-1-cyclopenten-1-yl]-2,4-pentadienoic Acid.

29. A process for preparing a compound according to claim 1,

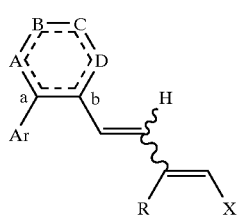

Formula 1 wherein

Ar, A, B, C, D, a, b, R and the dotted line (----) are as defined in claim 1;

which comprises reacting a compound of the formula ArBr or ArI with an alkyllithium, in an inert solvent, at −78° C. to +30° C., followed by adding $ZnCl_2$; to give a compound of formula:

ArZnCL reacting the ArZnCl with a compound of Formula II:

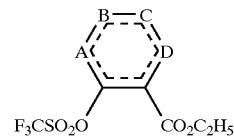

Formula II in the presence of a palladium(0) catalyst, in an inert solvent, at 10° C. to 60° C.; to obtain a compound of Formula III:

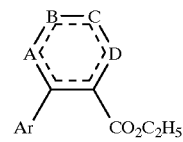

Formula III reducing the compound of Formula III with a hydride reducing agent in an inert solvent at 0° C. to 60° C.; to give a compound of Formula IV:

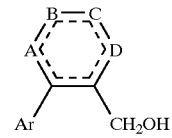

Formula IV reacting the compound of Formula IV with a trisubstituted phosphine hydrobromide to give a compound of Formula V:

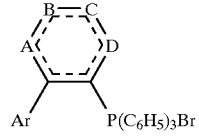

Formula V reacting the compound of Formula V with a base, in an inert solvent, at 0° C.; followed by addition of an aldehyde of the formula:

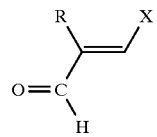

wherein R is as defined in claim 1; and

X is $CO_2R_8$ and $R_8$ is as defined in claim 1; to obtain a compound of Formula I.

30. A process for preparing a compound according to claim 1,

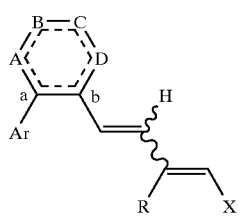

Formula 1 wherein Ar, A, B, C, D, a, b, R and the dotted line (---) are as defined in claim 1; and
X is —CHO;
which comprises reacting a compound of Formula I:

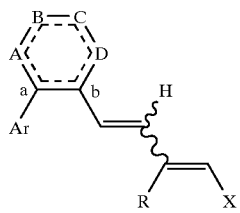

wherein Ar, A, B, C, D, a, b, R and the dotted line (---) are as defined in claim 1; and
X is —CO$_2$H or —CO$_2$R$_8$ and R$_8$ is as defined in claim 1;
with a hydride reducing agent, in an inert solvent, at 0° C. to 60° C.; to obtain a compound of Formula I wherein X is —CH$_2$OH; treating the compound of Formula I wherein X is CH$_2$OH with an oxidizing agent to give a compound of Formula I wherein X is —CHO.

31. A process for preparing a compound according to claim 1,

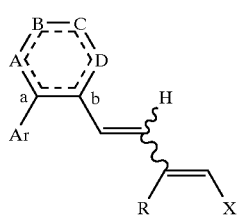

Formula 1 wherein Ar, A, B, C, D, a, b and R are as defined in claim 1; and X is —C(O)—NHR$_9$ wherein R$_9$ is as defined in claim 1;
which comprises reacting a compound of Formula I:

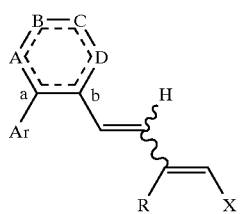

Formula 1 wherein Ar, A, B, C, D, a, b and R are as defined in claim 1; and X is —CO$_2$R$_8$ and R$_8$ is as defined in claim 1:

with a base under hydrolysis conditions at 30° C. to 100° C., followed by acidification with a mineral acid; to obtain a compound of Formula I wherein X is —CO$_2$H; reacting the compound of Formula I wherein X is —CO$_2$H with an activating reagent in an inert solvent, at 0° C. to 25° C.; to give an intermediate; adding an amine of the formula R$_9$NH$_2$ to the intermediate, wherein R$_9$ is as defined in claim 1; to obtain a compound of Formula I.

32. The process for preparing a compound according to claim 1:

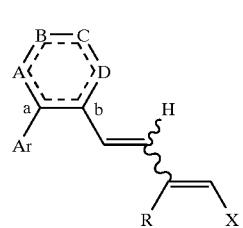

Formula 1 wherein Ar, A, B, C, D, a, b and R are as defined in claim 1; and X is —CO$_2$R$_8$ and R$_8$ is as defined in claim 1;
which comprises reacting a compound of Formula IV:

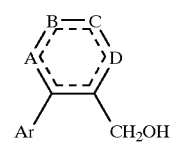

Formula IV wherein Ar and Y are as defined hereinabove; with an oxidizing agent, in an inert solvent, at 0° C. to 40° C.; to give a compound of Formula VIII:

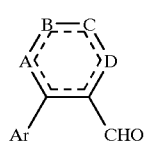

Formula VIII reacting the compound of Formula VIII with an ylide of the formula:

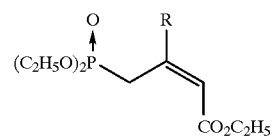

in the presence of a base in an inert solvent; to give a compound of Formula I.

33. A pharmaceutical composition which comprises a compound of claim 1 and a suitable carrier.

* * * * *